US012805927B2

(12) United States Patent
Eum

(10) Patent No.: US 12,805,927 B2
(45) Date of Patent: Nov. 24, 2026

(54) METHOD AND SYSTEM FOR TREATING HEMORRHOIDS

(71) Applicant: Minimax Medical (Nanjing) Co., Limited, Nanjing City (CN)

(72) Inventor: Jay J. Eum, Irvine, CA (US)

(73) Assignee: Minimax Medical (Nanjing) Co., Limited, Nanjing City (CN)

(*) Notice: Subject to any disclaimer, the term of this patent is extended or adjusted under 35 U.S.C. 154(b) by 536 days.

(21) Appl. No.: 18/271,074

(22) PCT Filed: Jan. 6, 2022

(86) PCT No.: PCT/US2022/011481
§ 371 (c)(1),
(2) Date: Jul. 6, 2023

(87) PCT Pub. No.: WO2022/150504
PCT Pub. Date: Jul. 14, 2022

(65) Prior Publication Data
US 2024/0050147 A1 Feb. 15, 2024

Related U.S. Application Data

(60) Provisional application No. 63/134,183, filed on Jan. 6, 2021.

(51) Int. Cl.
*A61B 1/32* (2006.01)
*A61B 1/00* (2006.01)
(Continued)

(52) U.S. Cl.
CPC ...... *A61B 18/1485* (2013.01); *A61B 1/00066* (2013.01); *A61B 1/31* (2013.01);
(Continued)

(58) Field of Classification Search
CPC ................ A61B 1/31; A61B 2018/005; A61B 2017/3452; A61B 1/32
See application file for complete search history.

(56) References Cited

U.S. PATENT DOCUMENTS

2008/0262511 A1* 10/2008 Delaney .................. A61B 1/31 600/184
2008/0275306 A1* 11/2008 Rebuffat ................. A61B 1/32 600/184
(Continued)

FOREIGN PATENT DOCUMENTS

WO WO-2004021874 A1 3/2004
WO WO-2005020931 A2 3/2005
WO WO-2020217223 A1 10/2020

OTHER PUBLICATIONS

Odet, WO 2020/217223, English Trasslation (Year: 2020).*
English translation of Odet WO 2020217223 A1 (Year: 2020).*

*Primary Examiner* — Jan Christopher L Merene
(74) *Attorney, Agent, or Firm* — M&B IP Analysts, LLC

(57) ABSTRACT

A system and method for treating hemorrhoids includes an anoscope assembly and a treatment probe. The anoscope assembly includes an elongated anoscope body and a sliding element. The anoscope body is insertable into the rectum of a patient. A main portion of the anoscope body has a longitudinal slot that functions as a window opening to trap hemorrhoids. A proximal portion of the anoscope body has handles thereon manipulatable by a user to adjust the cross-sectional area of the proximal portion. The sliding element is configured to slide through the proximal portion and through the longitudinal slot when the cross-sectional area of the proximal portion is sufficiently increased by a user by manipulation of the handles. Access and secure placement of the sliding element within the longitudinal slot is provided. The treatment probe operably connected to the
(Continued)

anoscope assembly is configured to provide energy to a hemorrhoid during treatment.

12 Claims, 18 Drawing Sheets

(51) Int. Cl.

| | |
|---|---|
| ***A61B 1/31*** | (2006.01) |
| ***A61B 18/08*** | (2006.01) |
| ***A61B 18/14*** | (2006.01) |
| *A61B 18/00* | (2006.01) |

(52) U.S. Cl.

CPC .............. *A61B 1/32* (2013.01); *A61B 18/082* (2013.01); *A61B 2018/005* (2013.01); *A61B 2018/00577* (2013.01); *A61B 2018/00982* (2013.01)

(56) References Cited

U.S. PATENT DOCUMENTS

| | | | | |
|---|---|---|---|---|
| 2009/0005647 | A1* | 1/2009 | Bozdag | A61B 1/31 600/235 |
| 2009/0259110 | A1* | 10/2009 | Bastia | A61B 17/0206 600/235 |
| 2019/0069923 | A1* | 3/2019 | Wang | A61B 8/0841 |
| 2021/0030424 | A1* | 2/2021 | Bhowmick | A61B 1/32 |

* cited by examiner

METHOD AND SYSTEM FOR TREATING HEMORRHOIDS

CROSS REFERENCE TO RELATED APPLICATIONS

This application is a national stage application of International Patent Application No. PCT/US2022/011481, filed on Jan. 6, 2022, which claims the benefit of U.S. Provisional Application Ser. No. 63/134,183 filed on Jan. 6, 2021, the entire contents of which are hereby incorporated herein by reference thereto.

BACKGROUND OF THE INVENTION

1. Field of the Invention

The present invention relates generally to systems and methods for treating hemorrhoids, and more particularly to advancements in anoscope assemblies used for such treatment.

2. Description of the Related Art

Hemorrhoids are swollen blood vessels in the rectum. There are two basic types of hemorrhoids: internal and external.

Internal hemorrhoids are swollen and inflamed veins far up in the rectum. Internal hemorrhoids cannot be seen or felt and usually are not painful due to the paucity in nerve endings in the upper portion of the rectum. While internal hemorrhoids are most commonly manifested by anal bleeding, they may prolapse or protrude outside the anal sphincter. Usually, prolapsed internal hemorrhoids may be gently pushed back into place in the rectum.

External hemorrhoids are swollen blood vessels in the anus and are usually manifested by pain as well as bleeding. When external hemorrhoids prolapse or protrude from the anal sphincter, blood clots sometimes form, causing an extremely painful condition known as thrombosis. While they usually disappear by themselves within about a week, thrombosed hemorrhoids may be removed by a physician or may be treated with a pain-reducing medication to reduce the pain.

It is believed that hemorrhoids are caused by the exertion of abdominal pressure on rectal veins, causing the veins to swell and become irritated. The abdominal pressure may be caused by a variety of factors and conditions, including obesity, pregnancy, prolonged standing or sitting, liver disease, straining during bowel movements, coughing, sneezing, vomiting, or holding the breath during physical activity. Hemorrhoids are largely preventable by the adoption of a high-fiber diet. On the other hand, person whose diet consists largely of low-fiber and processed foods tend to run the highest risk of developing hemorrhoids. Furthermore, inadequate fluid intake can contribute to the development of hemorrhoids by causing the development of hard stools, which irritate and inflame the rectal veins.

About half of population living in the United States will be afflicted with hemorrhoids at some point during their lives. Hemorrhoids most often strike people between the ages of 20 and 50. Some evidence indicates that "weak" veins, which are most susceptible to developing hemorrhoids, are inherited.

The present invention relates to applying heat energy by forms of conductive, resistive heating, and Radiofrequency heating. More particularly, the present invention relates to utilizing an innovative anoscope to position, monitor, and treat hemorrhoids. Lastly, the present invention utilized various probes to apply heat energy.

SUMMARY OF THE INVENTION

In one aspect the invention is embodied as a system for treating hemorrhoids includes an anoscope assembly and a treatment probe. The anoscope assembly includes an elongated anoscope body and a sliding element. The elongated anoscope body has a distal end and a proximal end. The anoscope body is configured to be insertable into the rectum of a patient. The elongated anoscope body includes a main portion and a proximal portion. The main portion has a longitudinal slot configured to function as a window opening to trap hemorrhoids. The proximal portion depends proximally from the main portion. The proximal portion has handles thereon configured to be manipulated by a user so as to adjust the cross-sectional area of the proximal portion. The sliding element is configured to slide through the proximal portion and through the longitudinal slot when the cross-sectional area of the proximal portion is sufficiently increased by a user by manipulation of the handles. This provides access and secure placement of the sliding element within the longitudinal slot. The treatment probe operably connected to the anoscope assembly is configured to provide energy to a hemorrhoid during treatment.

In an aspect the invention is a method for treating hemorrhoids that includes providing an anoscope assembly, providing a treatment probe, inserting the anoscope assembly into the rectum, inserting the treatment probe into the rectum, performing a treatment by utilizing the treatment probe, and removing the anoscope assembly. The anoscope assembly includes an elongated anoscope body and a sliding element. The elongated anoscope body has a distal end and a proximal end. The anoscope body is configured to be insertable into the rectum of a patient. The elongated anoscope body includes a main portion and a proximal portion. The main portion has a longitudinal slot configured to function as a window opening to trap hemorrhoids. The proximal portion depends proximally from the main portion. The proximal portion has handles thereon configured to be manipulated by a user so as adjust the cross-sectional area of the proximal portion. The sliding element is configured to slide through the proximal portion and through the longitudinal slot when the cross-sectional area of the proximal portion is sufficiently increased by a user by manipulation of the handles. This provides access and secure placement of the sliding element within the longitudinal slot. The treatment probe operably connected to the anoscope assembly is configured to provide energy to a hemorrhoid during treatment In one aspect, the ablating apparatus for use in treating a hemorrhoid of the present invention includes a combination of an anoscope, ablation catheter/paddle probe, dilator, and ground pad. The anoscope incorporates an adjustable window on the side of the scope body, which is positionable within an orifice. The window is closed during the insertion of the scope but is opened to receive the hemorrhoid tissue and applies clamping pressure onto the tissue. The adjustable window could further incorporate a return path for the RF signal and/or a temperature measuring element to monitor the tissue temperature. The ablation catheter includes an ablating element for treating the tissue and a temperature measuring element for monitoring the ablating element during treatment. The dilator includes a hollow lancing shaft within which an ablation catheter is situated. The dilator sheath (a hollow lancing shaft) has a central passage for the drainage of fluids. The ablation catheter, the dilator, and the anoscope is controlled or monitored by a control unit that displays the temperatures from the temperature measuring elements of the ablating apparatus and supplies energy to the ablating element of the catheter.

The ablating element may use any number of modalities that are suitable for ablating a hemorrhoidal tissue. The ablating element may be a contact catheter that can be used without the dilator. The ablating element may be a heating element that does not require electricity to flow from the ablation element to the body. Examples of ablation elements include but are not limited to a resistive heater, a radiofrequency electrode, a laser heating fiber, and a microwave antenna probe. If it is a resistive heater, it may be, for example, a resistive wire heater, semi-conductor material heater, or resistive sheath heater. The energy source may be, for example, direct current, alternating current, or radiofrequency current. The ablating element may be a cooling element, such as a cryosurgical device.

The ablating apparatus can be used with a multi-functional control system for controlling the overall ablative process, including, for example, monitoring the temperature of the ablating device and surrounding tissue, timing the ablation, controlling the energy level to the ablating device, and controlling the energy path from the ablation catheter to anoscope and/or to ground pad.

Other objects, advantages, and novel features will become apparent from the following detailed description of the invention when considered in conjunction with the accompanying drawings.

DETAILED DESCRIPTION OF THE INVENTION

Figure 1:
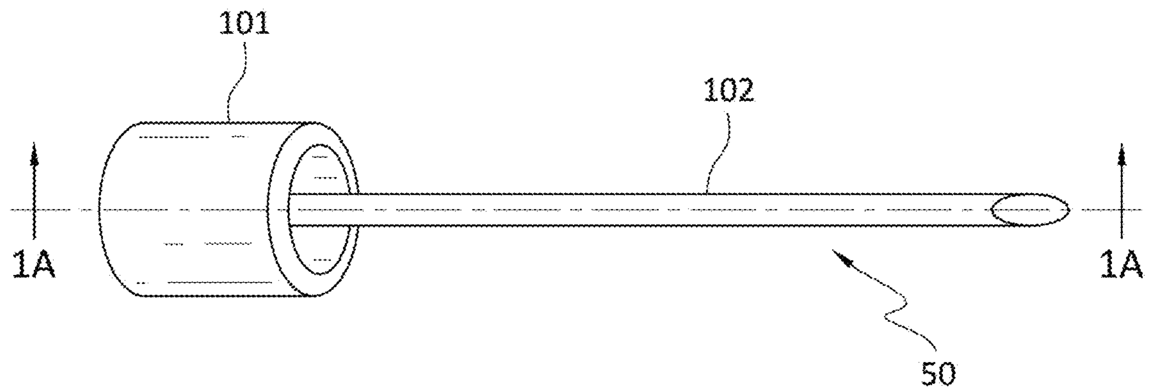
FIG. 1 is a perspective view of an embodiment of the dilator assembly of the system for treating hemorrhoids of the present invention.
Figure 1A:
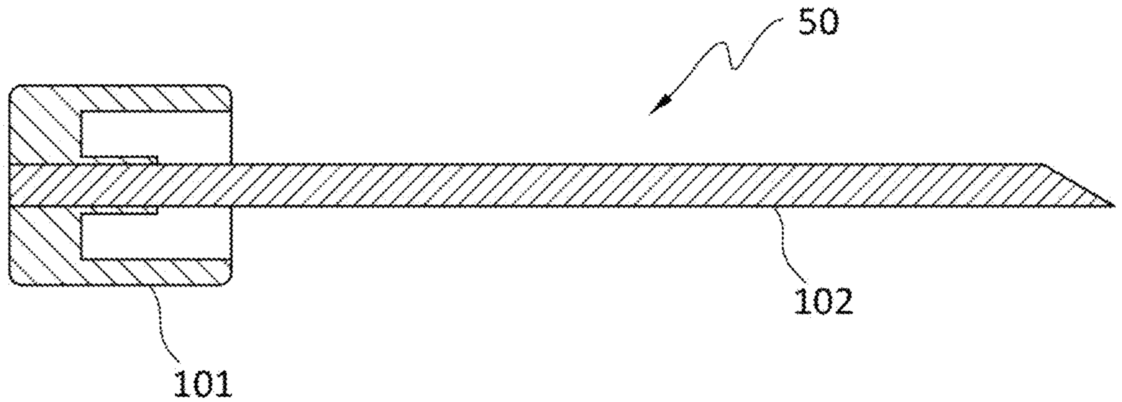
FIG. 1A is a sectional view of the dilator assembly taken along line 1A-1A of FIG. 1.

Referring to FIGS. 1 and 1A, dilator assembly 50 includes a dilator connector 101 connected to a dilator needle 102.

The length and diameter of the dilator needle 102 are configured with dilator sheath 104 such that the needle 102 has to fit inside of the sheath 104 and the needle 102 has to extend beyond the end of the sheath 104 by the length of the ablation zone formed by ablation catheter 52. The dilator may be formed of rigid materials, for example, but not limited to stainless steel and titanium. The tip of the dilator needle 102 has a smaller diameter than the diameter of the proximal end of the catheter for penetration into tissues. Examples of the tips are, for example, but not limited to, trocar and needlepoint tips.

Dilator connector 101 is designed to mate with sheath connector 103. Dilator connector 101 is attached to dilator 102. The dilator connector 101 may be formed with a dielectric material, for example, but not limited to polycarbonate, ABS, and Nylon, etc.

Figure 2:
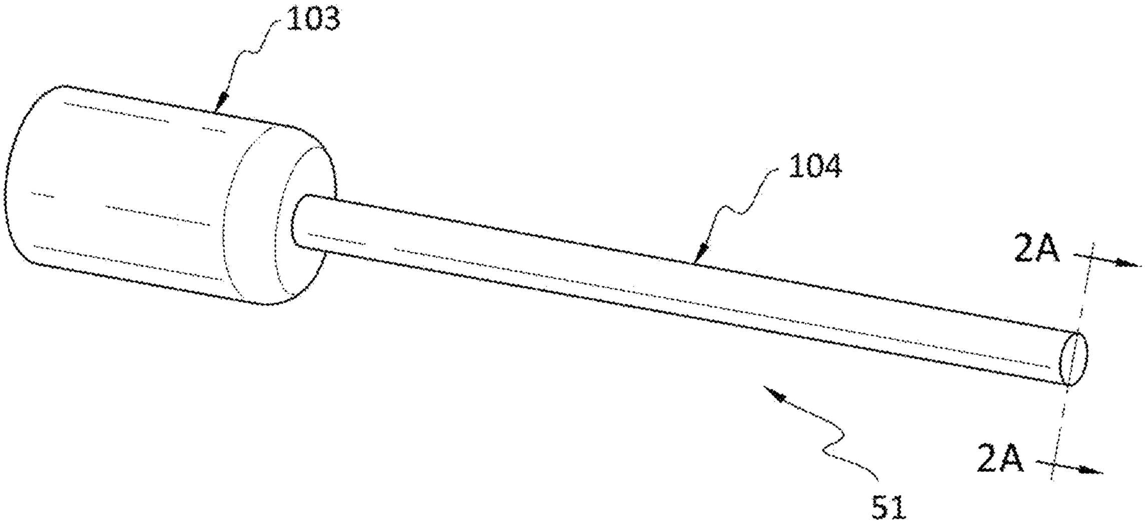
FIG. 2 is a view of an embodiment of the dilator sheath assembly of the system for treating hemorrhoids of the present invention.
Figure 2A:
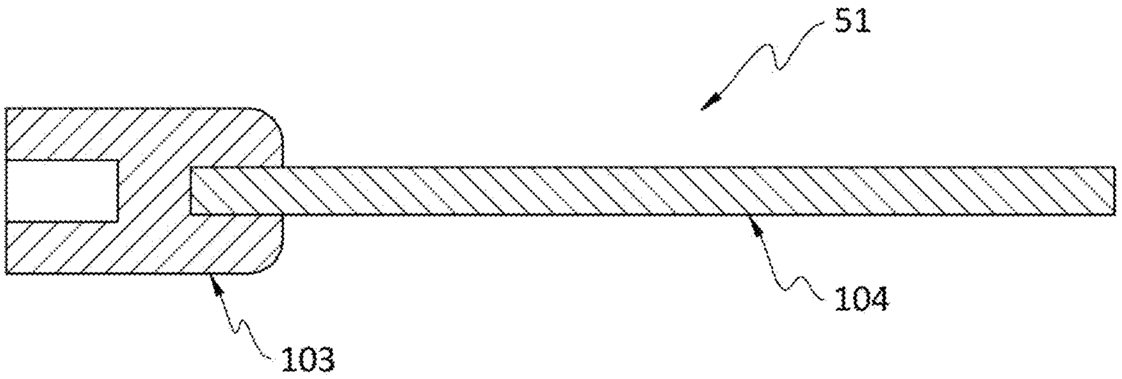
FIG. 2A is a sectional view of the dilator sheath assembly taken along line 2A-2A of FIG. 2.

Referring now to FIGS. 2 and 2A, dilator sheath assembly 51 includes dilator sheath connector 103 and dilator sheath 104. There is a channel formed in the middle of the dilator connector 103, which extends along the length of the dilator sheath 104, allows dilator 50 to be positioned inside of the sheath assembly 51. The dilator connector 101 mates with dilator sheath connector 103. The dilator connector 103 is designed to mate with the connector of syringe 129. The dilator sheath 104 may be formed with high dielectric and rigid material, for example, but not limited to mylar and PTFE. The dilator sheath connector 103 may be formed with a dielectric material, for example, but not limited to polycarbonate, ABS, and Nylon, etc.

Figure 3:
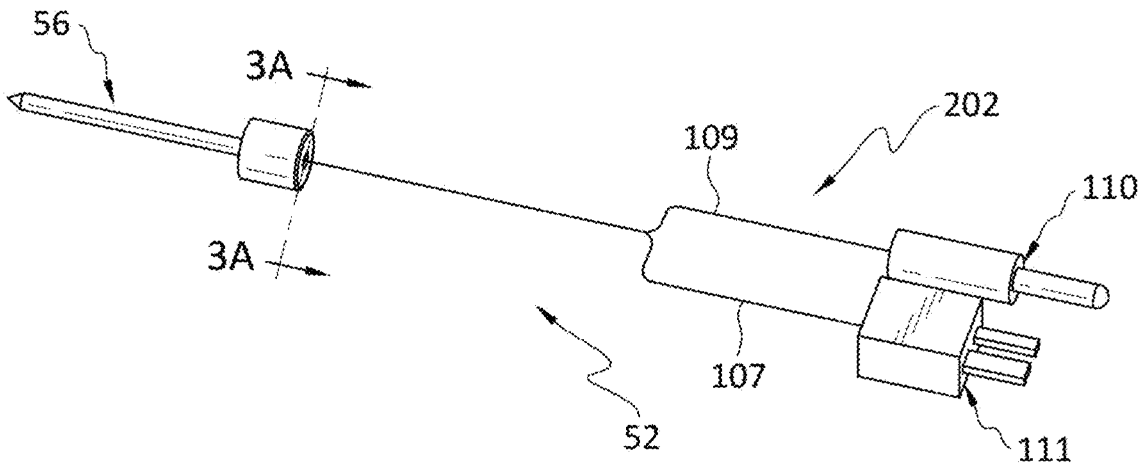
FIG. 3 is a perspective view of an embodiment of an ablation element (probe) of the system for treating hemorrhoids of the present invention, embodied as an ablation catheter.
Figure 3A:
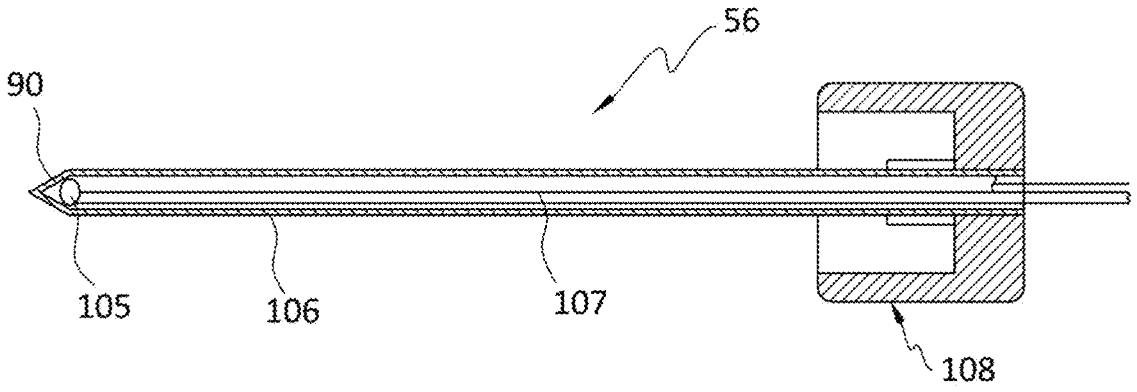
FIG. 3A is a sectional view of the ablation catheter, taken along line 3A-3A of FIG. 3.
Figure 3B:
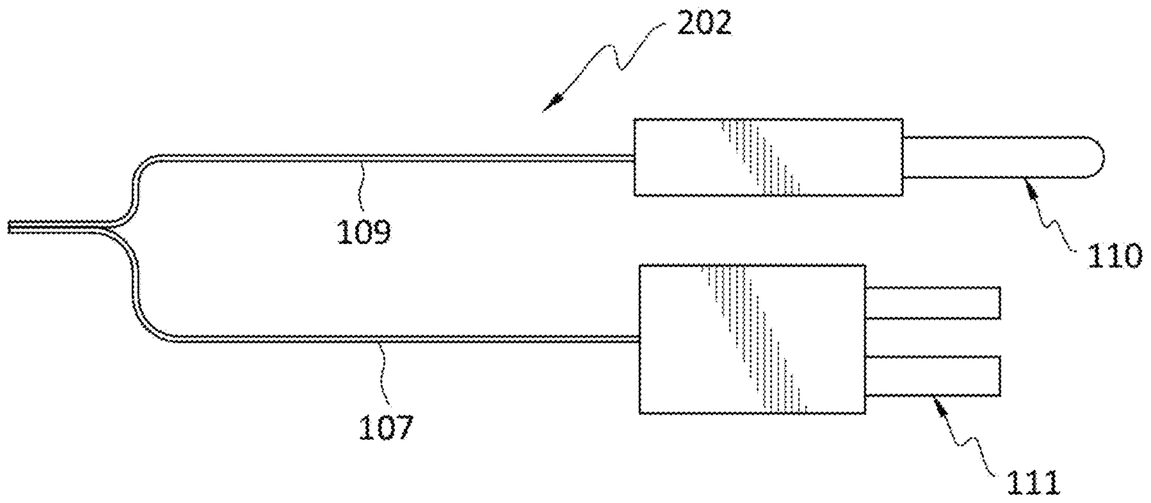
FIG. 3B is a schematic view of the ablation catheter assembly connectors.
Figure 4:
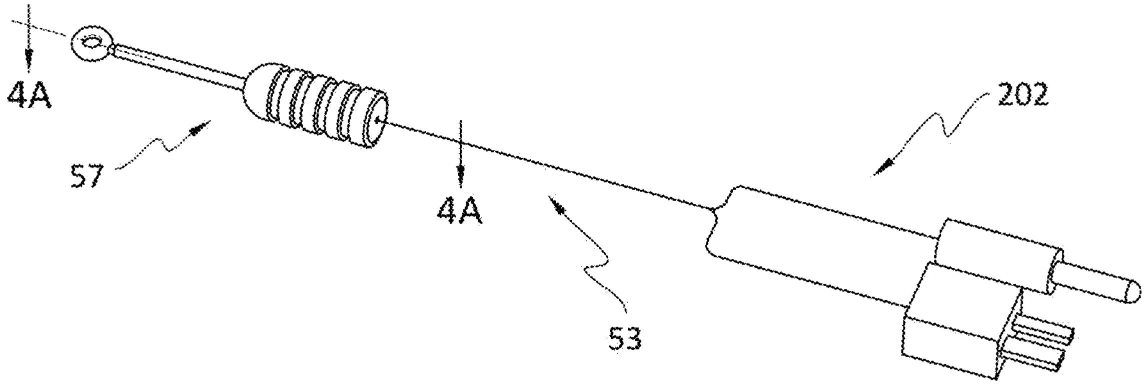
FIG. 4 is a perspective view of an embodiment of the paddle ablation probe assembly.
Figure 4A:
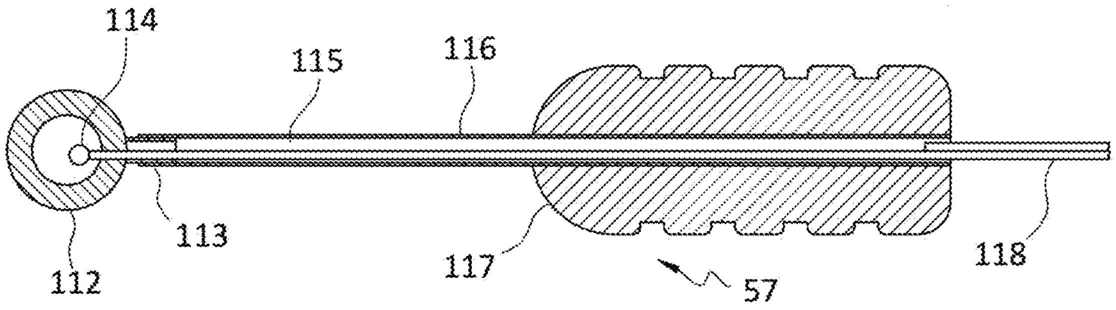
FIG. 4A is a sectional view of paddle ablation probe.
Figure 4B:
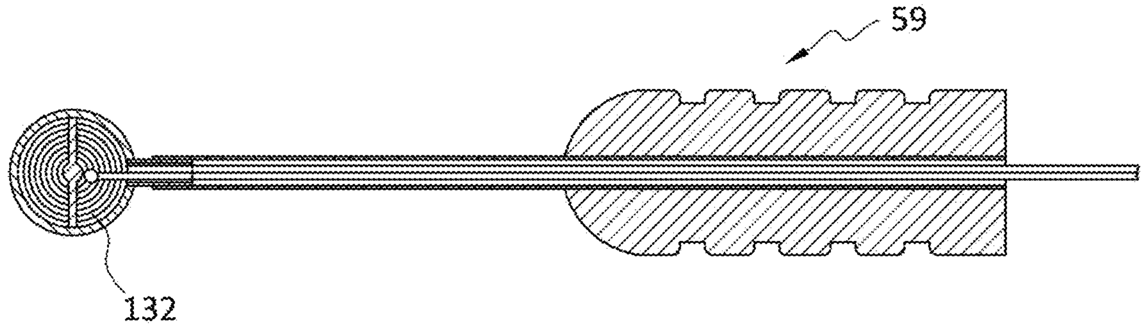
FIG. 4B is a sectional view of another embodiment of paddle ablation probe.
Figure 4C:
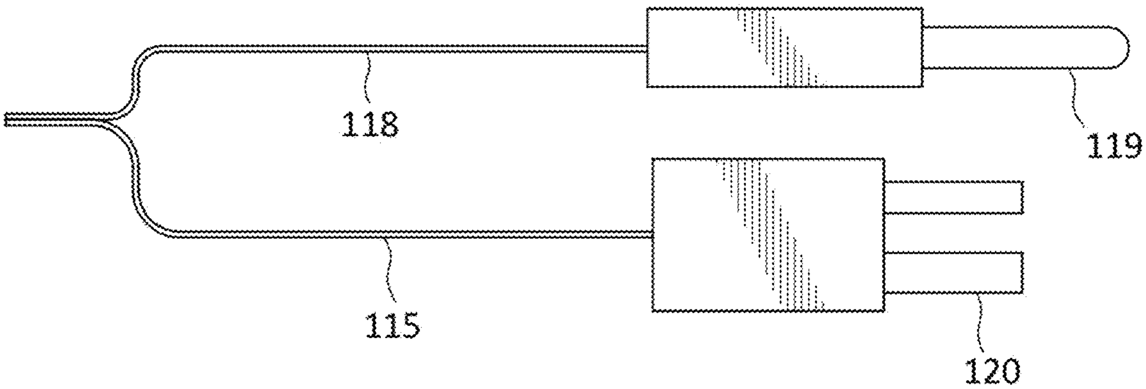
FIG. 4C is a view of paddle probe connectors.
Figure 5:
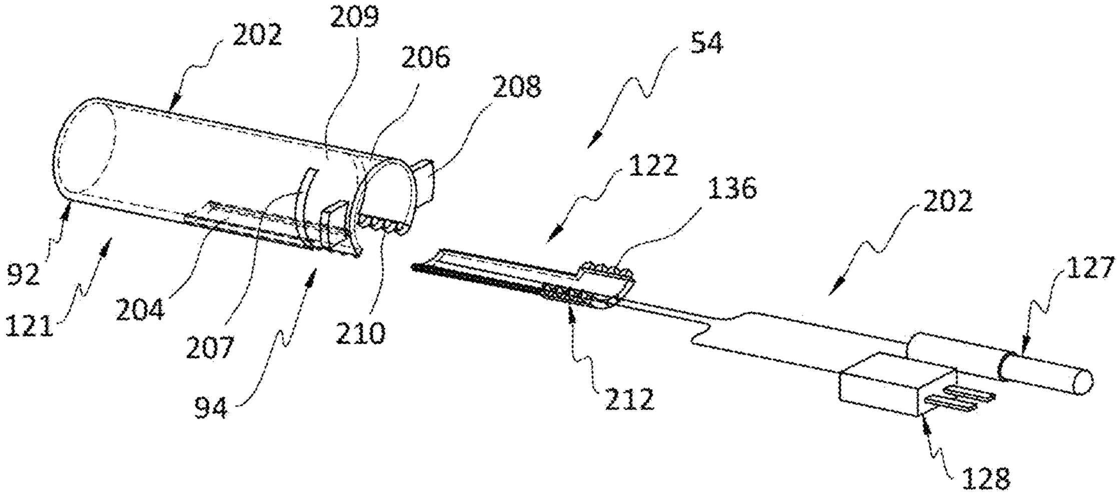
FIG. 5 is a view of the anoscope assembly.
Figure 5A:
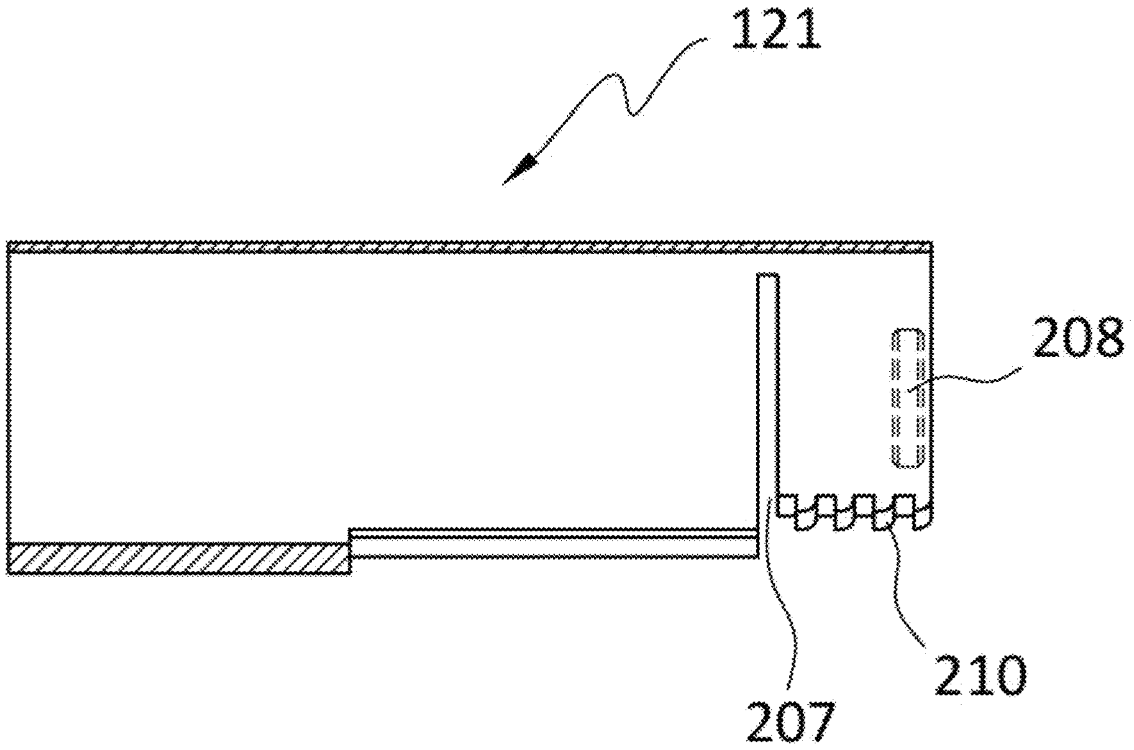
FIG. 5A is a sectional view of the anoscope body.
Figure 5B:
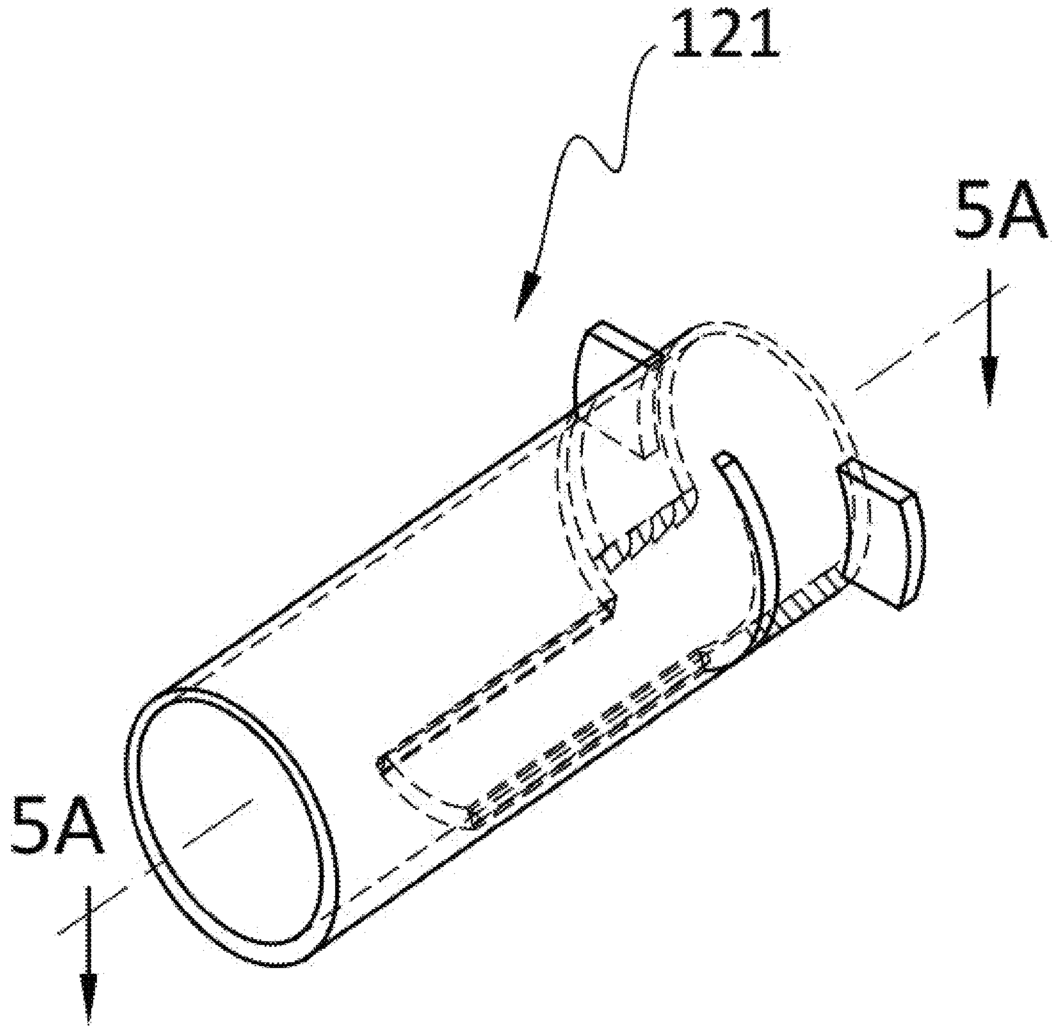
FIG. 5B is another view of the anoscope body.
Figure 5C:
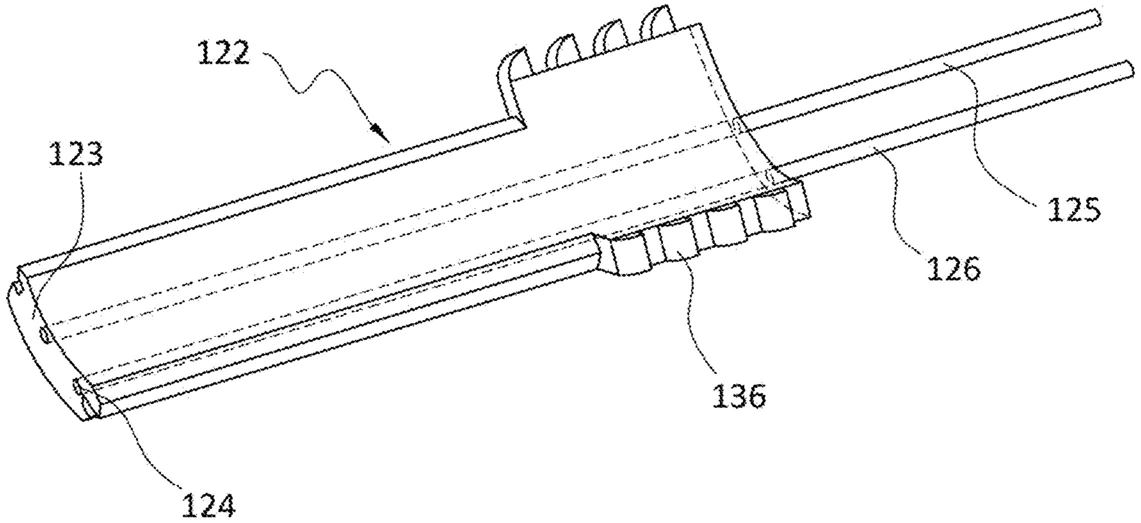
FIG. 5C is a view of the anoscope sliding window.
Figure 5D:
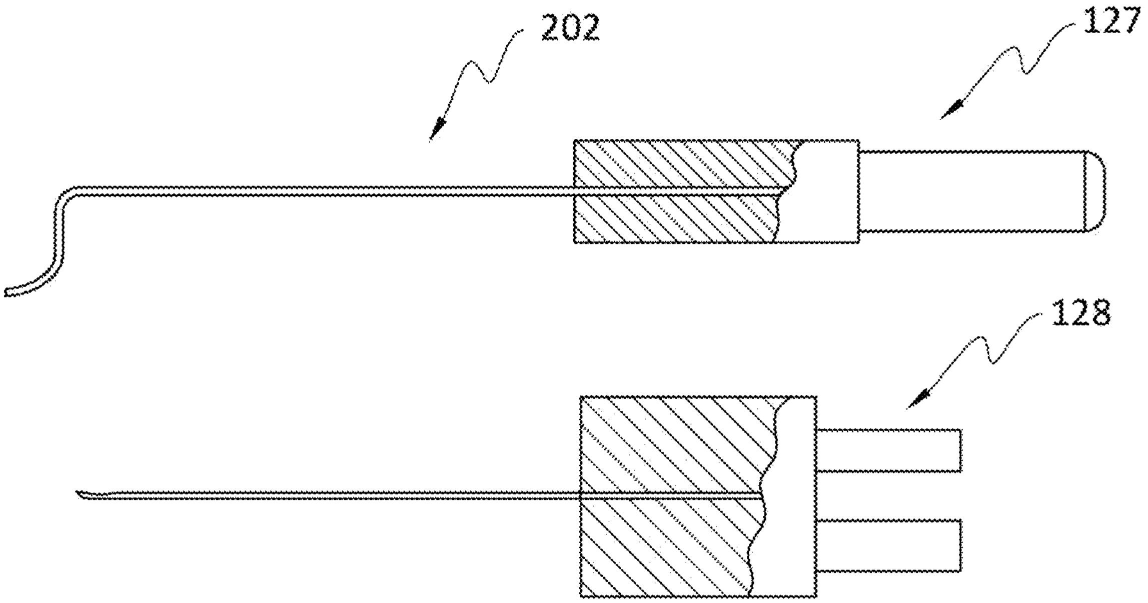
FIG. 5D is a sectional view of sliding window connectors.

Referring to FIGS. 3, 3A, and 3B, ablation catheter assembly 52 includes and ablation catheter element 56. Ablation catheter element 56 includes ablation catheter temperature sensor 105, ablation catheter sheath 106, ablation catheter temperature sensing cable 107, and ablation catheter connector 108. the ablation catheter assembly 52 also includes ablation catheter connectors including ablation catheter power cable 109, an ablation catheter power connector 110, and an ablation catheter temperature sensing connector 111, cable 107, cable 109, connector 110, and connector 111, collectively define a connector system designated generally as 202.

The ablation catheter temperature sensor 105 is preferably attached near the tip 90 of the inside of the ablation catheter sheath 106. The temperature sensor 105 is used to monitor the maximum temperature reached at the ablation zone of the ablation catheter 52. For the safety of the ablation, it is ideal, not only to measure the temperature at the extent of the targeted hemorrhoid 128, but also to measure the temperature at the energy source to prevent the over treatment of the tissues adjacent to the catheter tip 90 while the other tissues of hemorrhoid away from the tip 90 has not reached the temperature. The temperature sensor 105 can be utilized using different temperature measuring modalities, for example, but not limited to thermocouples, thermistors, and RTDs (Resistance Thermometer Detectors).

Figure 6A:
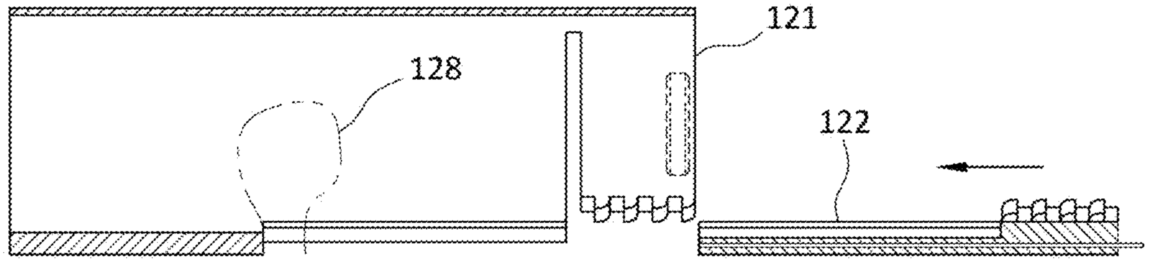
FIG. 6A-6G are views of procedural steps for using an ablation catheter.
Figure 6B:
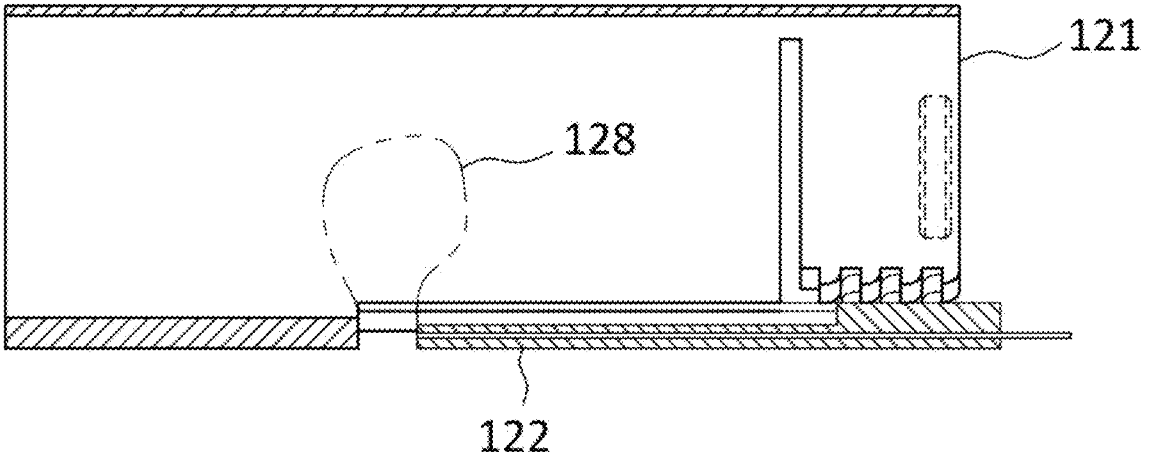
Figure 6C:
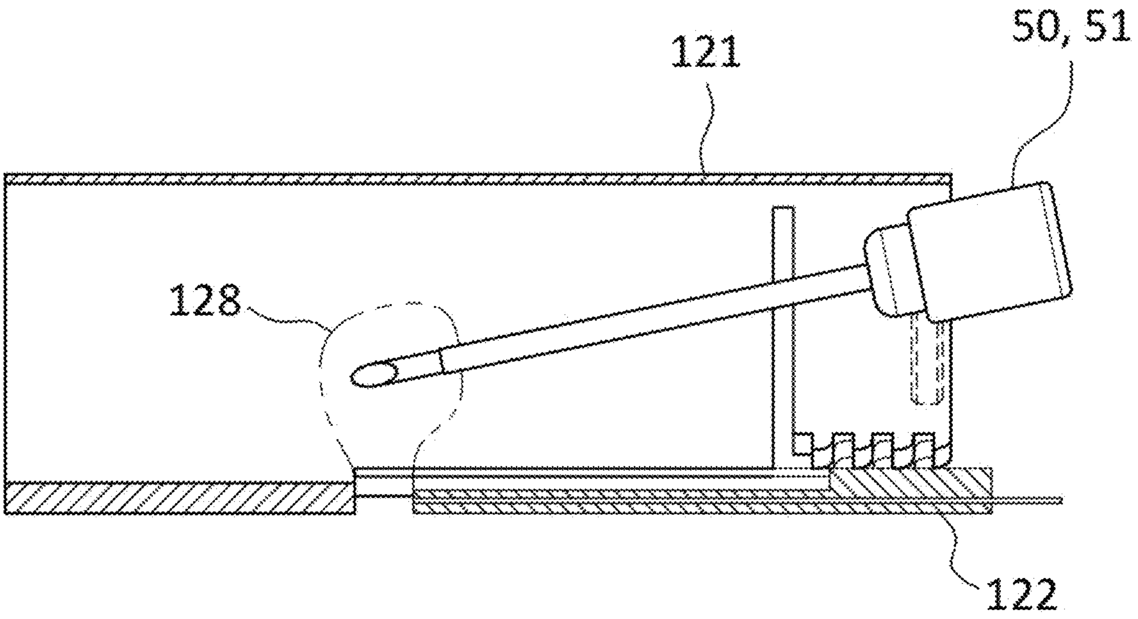
Figure 6D:
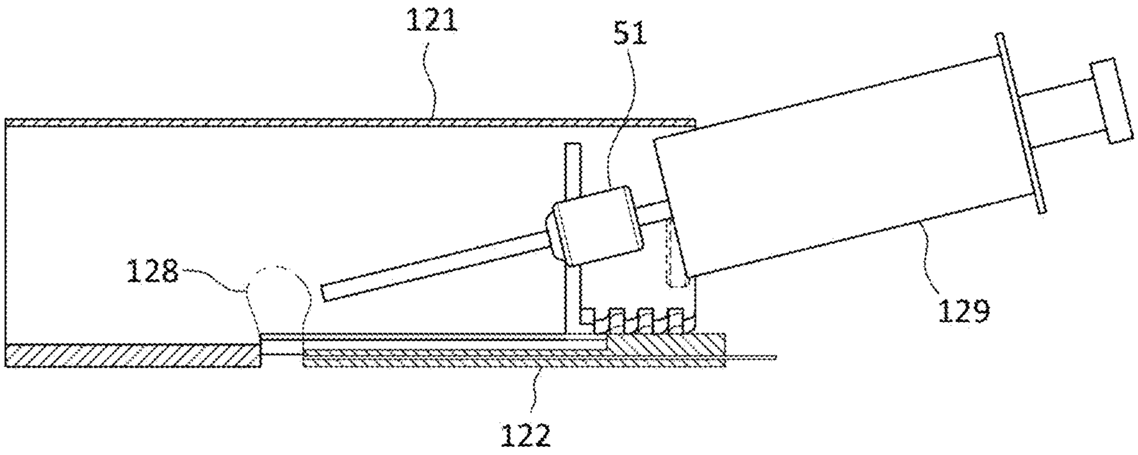
Figure 6E:
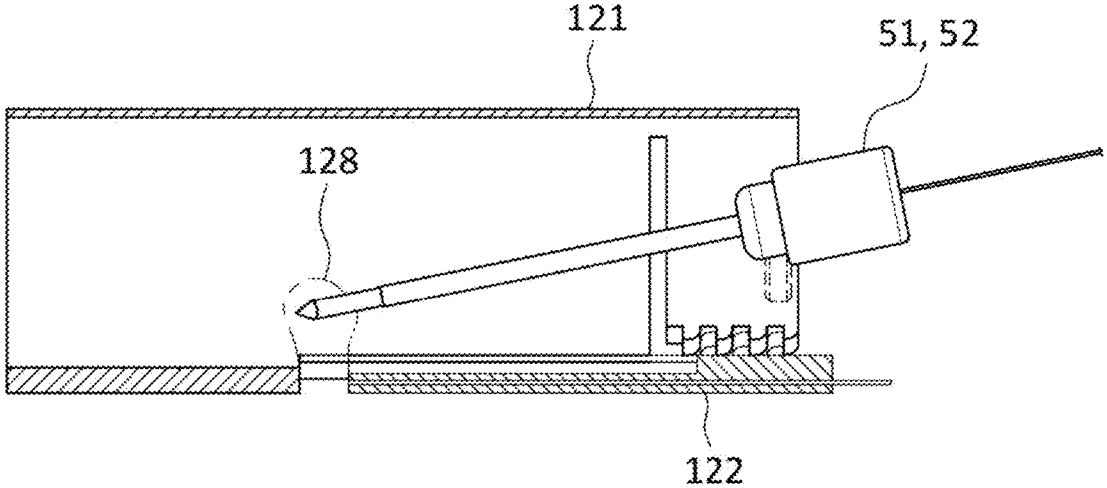
Figure 6F:
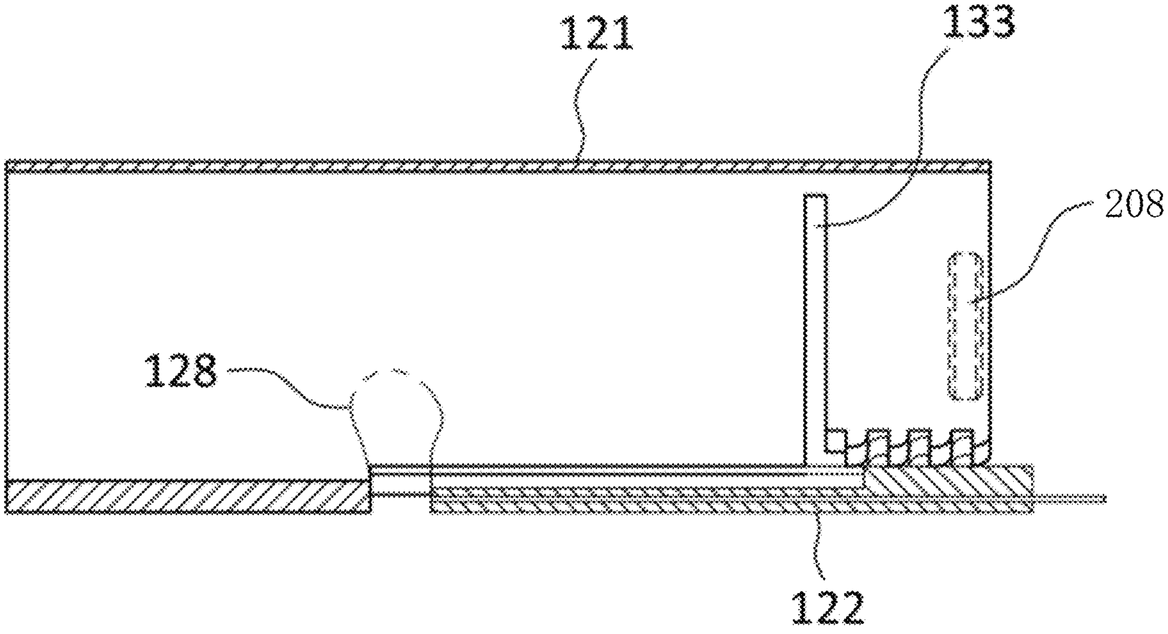
Figure 6G:
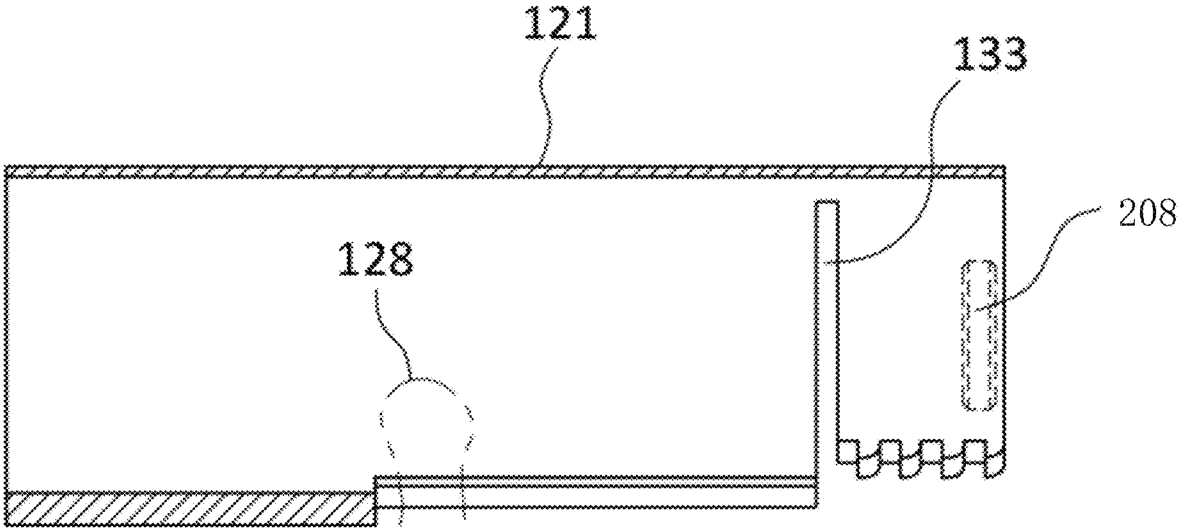
Figure 7A:
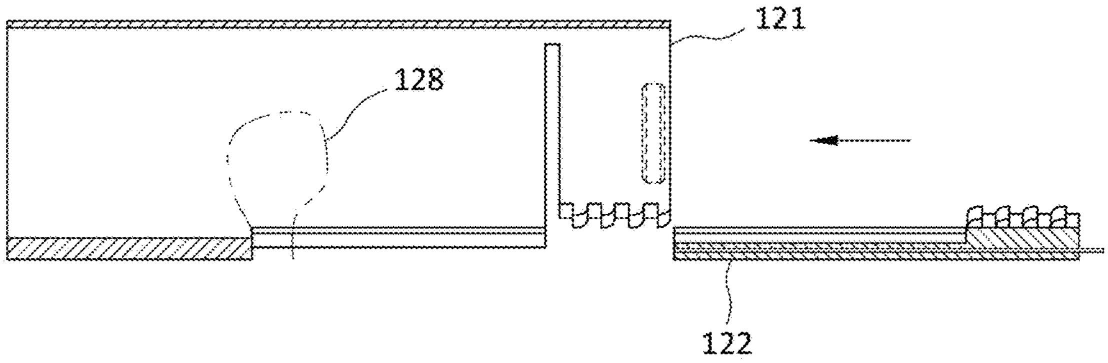
FIG. 7A-7E are views of procedural steps for using a paddle ablation probe.
Figure 7B:
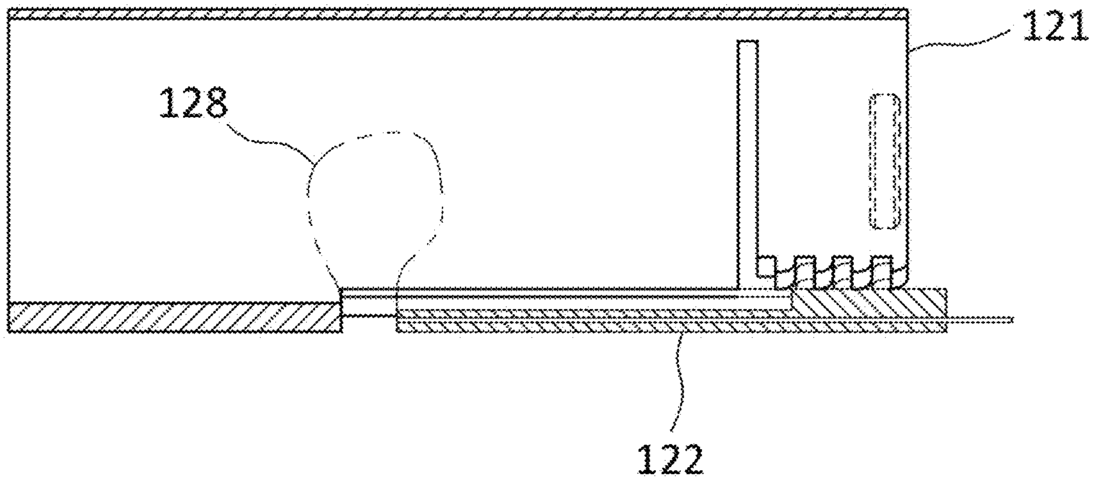
Figure 7C:
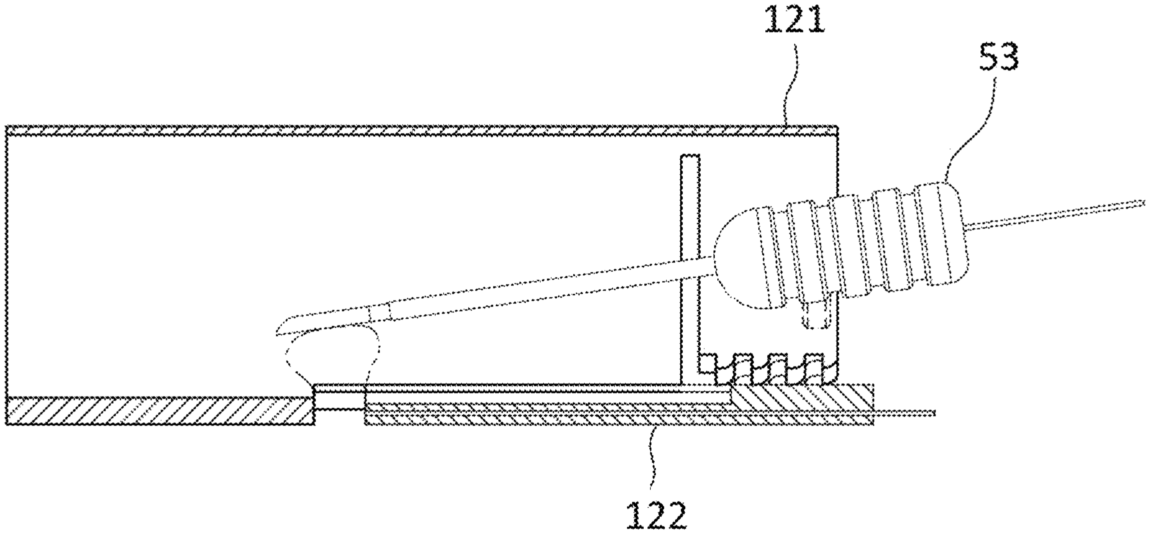
Figure 7D:
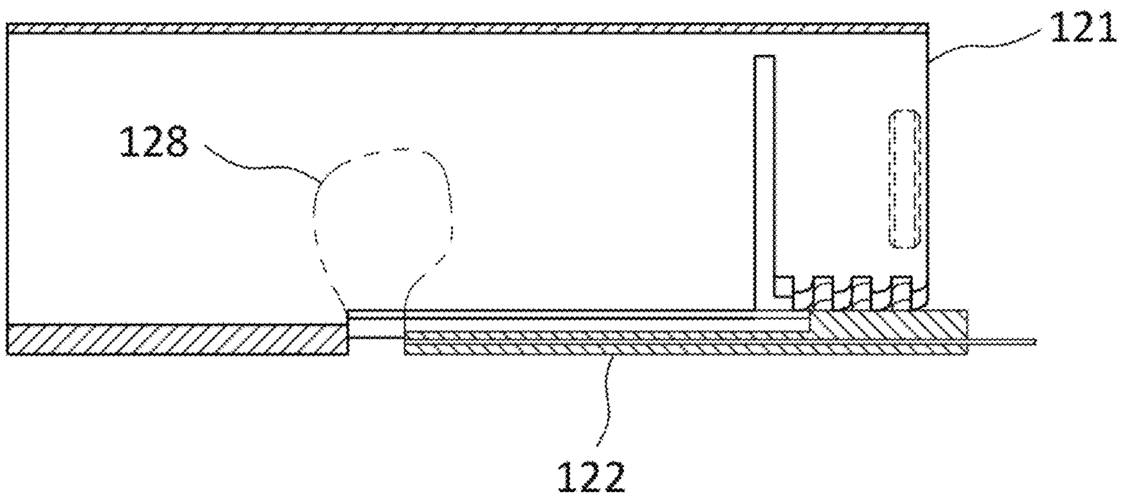
Figure 7E:
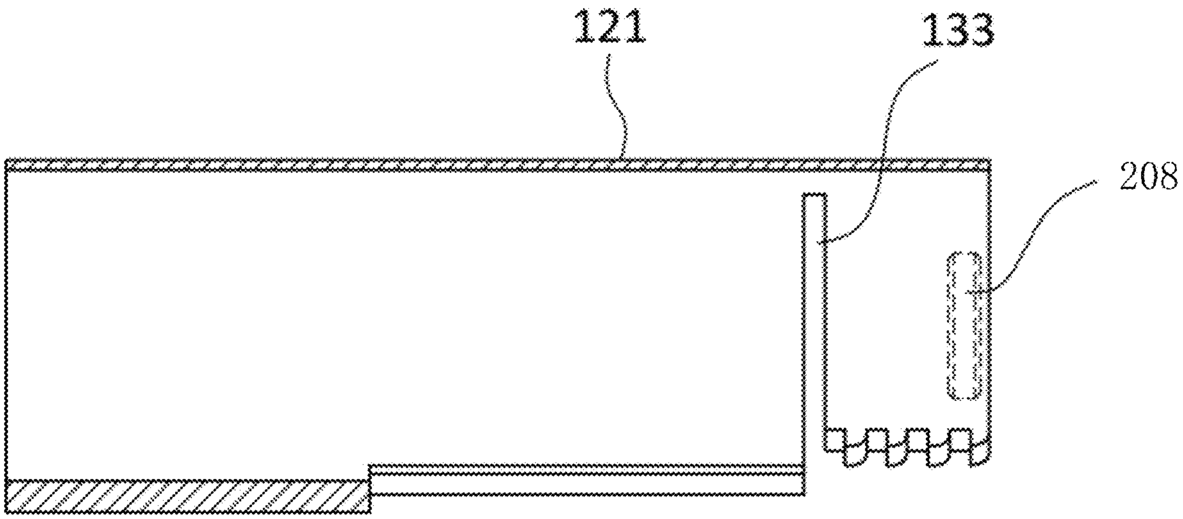

The ablation catheter sheath 106 is attached to the ablation catheter connector 108 and extends therefrom. The ablation catheter sheath 106 fits inside of the dilator sheath element 104 and extends beyond the end of the dilator sheath element 104. The outside surface of the ablation catheter sheath 106 touches hemorrhoid 128 (see, for example, FIG. 6E). For one of the embodiments that utilizes RF power flow from the ablation catheter to the hemorrhoid tissue to deliver heat, the ablation catheter sheath is formed from electrically conductive and biocompatible materials, for example, but not limited to stainless steel and titanium. Preferably, the tip of the ablation catheter sheath has a smaller diameter than the diameter of the proximal end of the catheter. Examples of the tips are, for example, but not limited to, trocar and needlepoint tips. If the user utilizes a dilator to penetrate the hemorrhoid before inserting the ablation catheter element 56 into hemorrhoid, the tip 90 of the ablation catheter sheath 106 can be blunt.

One end of the ablation catheter temperature sensing cable 107 is attached to the temperature sensor 105. The other end of the temperature sensing cable is attached to the temperature sensor connector 111. The temperature sensing cable 107 is positioned inside of the catheter probe sheath 106 for the portion that extends along the ablation probe sheath. If a thermocouple is used for temperature sensor 105, temperature sensing cable 107 and temperature sensor 105 is the same assembly of a thermocouple junction wire. If the temperature sensor 105 is a thermistor or RTD, etc., the temperature sensing cable comprises a pair of electrical wires insulated from each other.

The ablation catheter connector 108 is connected to the ablation catheter sheath 106 and configured to mate with the dilator sheath assembly 51. The ablation catheter connector 108 can be formed with dielectric materials, for example, but not limited to polycarbonate, ABS, and Nylon, etc.

One end of the ablation catheter power cable 109 is connected to the ablation catheter power connector 110. For the embodiment of utilizing RF energy, the other end of the catheter power connector 109 is connected to the ablation catheter sheath 106. The ablation catheter power cable 109 is positioned inside of the catheter probe sheath 106 for the portion that extends along the ablation probe sheath. The ablation catheter power cable is a single or multiple conduction cables.

In an embodiment utilizing thermocouple wires as the ablation catheter temperature sensor 105, temperature sensing connector 111 is a thermocouple connector that matches the compound of the thermocouple wire used. In an embodiment using a thermistor or RTD as temperature sensor 105, temperature sensing connector 111 is an electrical connector. One end of the temperature connector is attached to the thermocouple cable 107, and the other end plugs into the system 55.

Figure 8:
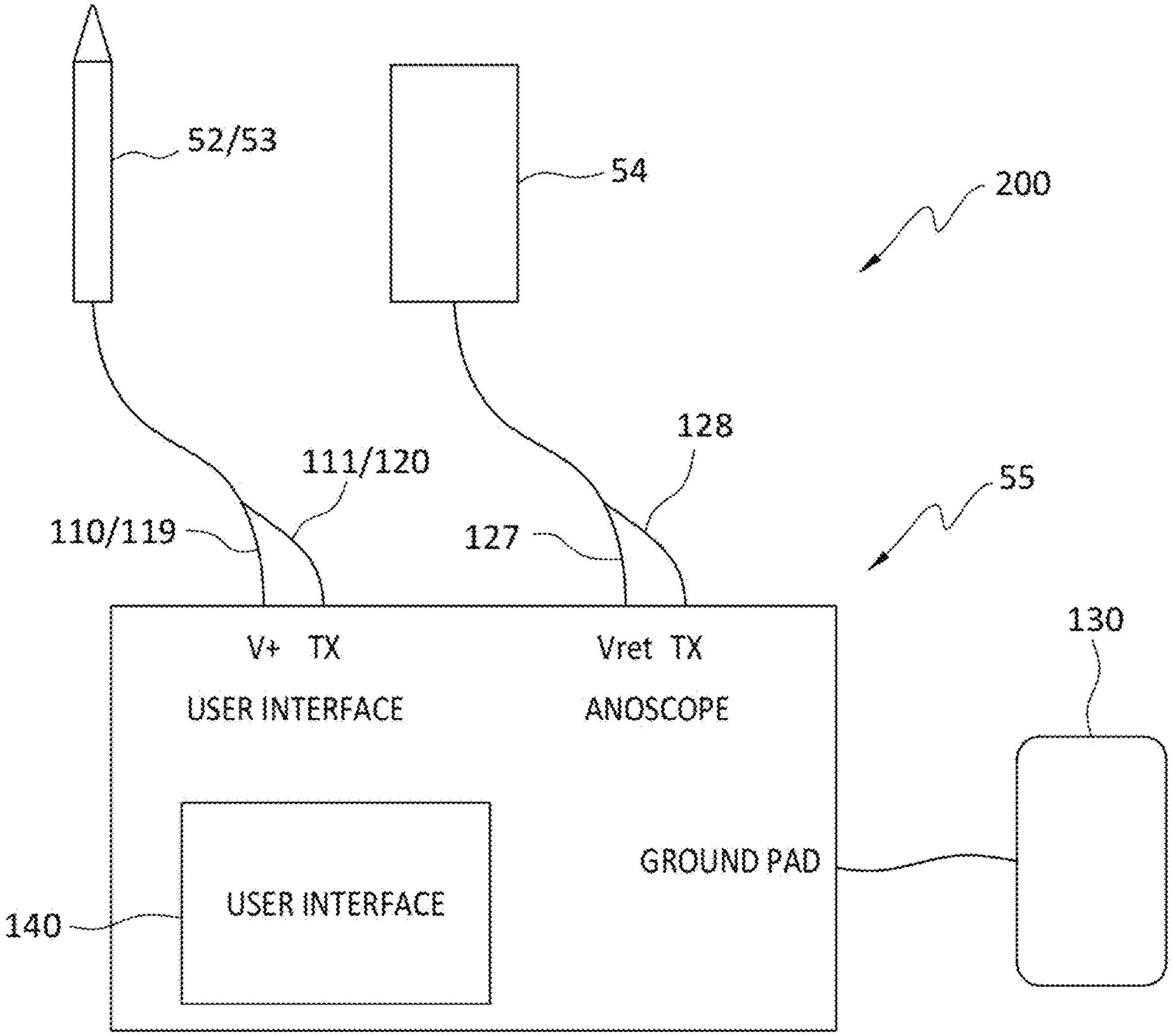
FIG. 8 is a block diagram of the overall system.

One end of the ablation catheter power connector 110 is connected to the ablation catheter power cable 109, and the other end of the power connector plugs into the system 55(see FIG. 8). The ablation catheter power connector 110 has a portion that is electrically conductive that mates to electrically conductive material located inside of the system 55. The conductive material in the power connector 110 is preferably not exposed to the user. Outside housing of the power connector 110 can be formed with dielectric materials, for example, but not limited to polycarbonate, ABS, and Nylon, etc.

Referring to FIGS. 4, 4A, 4B, and 4C, a paddle ablation probe assembly 53 includes a paddle ablation probe element 57. Paddle ablation probe element 57 includes paddle ablation disk 112, paddle ablation probe sheath 113, paddle ablation probe temperature sensor 114, paddle ablation probe sensor cable 115, paddle ablation probe insulation sheath 116, paddle ablation probe handle 117. The paddle ablation probe assembly 53 also includes a paddle ablation power cable 118, paddle ablation probe power connector 119, and paddle ablation probe temperature connector 120. In another embodiment (see FIG. 4B) the paddle ablation probe 59 includes resistive material 132 to apply heat energy to hemorrhoid.

The paddle ablation disk 112 is attached to the paddle ablation probe sheath 113. The paddle ablation disk 112 is designed to fit inside of the anoscope body 121 and apply operable contact and pressure to hemorrhoid 128. One surface of the paddle ablation disk is designed to touch hemorrhoid 128 during treatment. The other side could also be designed to be used during treatment but it's not necessary. It is preferable to have the side designed to treat the hemorrhoid be flat, but it could also be arched or be different shapes to increase the contact area between the paddle ablation probe surface to the hemorrhoid. If the other side is not utilized for treatment, it could be designed to have a different shape and surface than the treatment side, for example, but limited to dome shape, triangular shape, etc. For one of the embodiments that utilizes RF power flow from the paddle ablation probe 53 to the hemorrhoid tissue to deliver heat, the surface that delivers energy is formed with electrically conductive and biocompatible materials, for example, but not limited to stainless steel and titanium. The rest of the body, including the side that is not designed to deliver energy, can be formed using biocompatible and non-conductive materials, for example, but not limited to various plastics such as polycarbonate, ABS, and nylons. For the other embodiment that utilizes resistive material to apply heat, the surface that delivers energy can be formed with biocompatible, thermally conductive, and electrically non-conductive materials.

The paddle ablation probe sheath 113 is attached to paddle ablation probe disk 112 and paddle ablation probe housing (handle) 117. The diameter is narrower than the height of the paddle ablation probe disk 112. It is preferable to have the diameter as small as possible for better viewing of the treatment area during treatment, but the paddle ablation sheath 113 has to be sufficiently rigid for the user to apply operable contact pressure to the hemorrhoid during treatment. The outside surface of the paddle ablation probe sheath 113 is not necessarily touching hemorrhoids during treatment, but it is preferable to make the sheath bio-biocompatible.

The paddle ablation probe temperature sensor 114 is located inside of the paddle ablation probe disk 112. The temperature sensor 114 is used to monitor the maximum temperature reached at the ablation zone of the paddle ablation probe 53. For the safety of the ablation, it is ideal, not only to measure the temperature at the extent of the targeted hemorrhoid 128, but to also measure the energy source to control the heating of the tissue adjacent to the ablation zone. The temperature sensor 105 can be utilized using different temperature measuring modalities, for example, but not limited to thermocouples, thermistors, and RTDs.

One end of the paddle ablation probe temperature sensing cable 115 is attached to the paddle ablation probe temperature sensing sensor 114. The other end of the temperature sensing cable is attached to the paddle ablation probe temperature sensor connector 120. The paddle ablation probe temperature sensing cable is positioned inside of the paddle ablation probe sheath 113 for the portion that extends along the paddle ablation probe sheath. If a thermocouple is used for temperature sensor 114, temperature sensing cable 115 and temperature sensor 114 is the same assembly of a thermocouple junction wire. If the temperature sensor is a thermistor or RTD, etc., the temperature sensing cable is a pair of electrical conductors insulated from each other.

One end of the paddle probe handle 117 is attached to the paddle probe sheath 113 and paddle probe insulator sheath 116. The other end of the paddle probe handle 117 is attached to the paddle probe temperature cable 115 and power cable 118. For the embodiment that utilizes RF energy for treatment, attachment of the paddle probe sheath 113 and paddle probe power cable 118 can be done inside of the paddle probe handle 117. The housing of the probe handle 117 can be formed with dielectric materials, for example, but not limited to polycarbonate, ABS, and Nylon, etc.

One end of the paddle ablation probe power cable 118 is connected to the paddle ablation probe power connector 119. The paddle ablation probe power cable 118 is located inside of the paddle ablation probe sheath 113 for the portion that extends along the paddle ablation probe sheath. For the embodiment of utilizing RF energy, the other end of the paddle ablation probe power connector 119 is connected to the paddle ablation probe sheath 113. The paddle ablation probe power cable 118 may be a single cable or use multiple conduction cables. In another embodiment utilizing resistive material 132 to deliver heat energy, one end of the paddle ablation probe power cable 118 is attached to the resistive material 132. The other end is attached to the paddle ablation probe power connector 119.

For another embodiment using conductive heat to deliver heat energy to hemorrhoid 128, resistive material 132 is utilized. The resistive material 132 is located at the inside wall of the paddle ablation probe disk 112. Several different materials can be used for resistive material 132, for example, but not limited to resistive wire, thermocouple wire, and semi-conductor materials. In an embodiment using thermocouple wire as resistive material, temperature sensor 114, resistive material 132, paddle ablation probe power cable 118, and paddle ablation probe temperature sensor cable 119 can be a single assembly of one thermocouple wire.

For an embodiment using RF energy to deliver heat energy and using paddle ablation probe sheath 113 to conduct electricity to the paddle ablation probe disk 112, paddle ablation probe insulation sheath 116 is utilized to prevent electrical conduction from the probe sheath 113 to surrounding tissues and/or to the user. The paddle ablation probe insulation sheath 116 is positioned outside of the paddle ablation probe sheath 113 along the length of the sheath. The paddle ablation probe insulation sheath can be formed using electrically insulating materials such as, but not limited to, mylar, PTFE, Nylon, and PVC, etc.

In an embodiment utilizing thermocouple wires as the paddle probe temperature sensor 114, temperature sensing connector 120 is a thermocouple connector that matches the compound of the thermocouple wire used. In an embodiment using a thermistor or RTD as temperature sensor 114, temperature sensing connector 120 is an electrical connector. One end of the thermocouple connector is attached to the temperature cable 115, and the other end plugs into the system 55.

One end of the ablation catheter power connector 119 is connected to the paddle power cable 118, and the other end of the power connector plugs into the system 55. The paddle power connector 119 has a portion that is electrically conductive that mates to electrically conductive material located inside of the system 55. The conductive material in the power connector 119 is preferably not exposed to the user. Outside housing of the power connector, 119 can be formed with dielectric materials, for example, but not limited to polycarbonate, ABS, and Nylon, etc.

Referring to FIGS. 5, 5A, 5B, 5C, and 5D, an anoscope assembly 54 includes an elongated anoscope body 121 having a distal end 92 and a proximal end 94. The anoscope body includes a main portion 202 having a longitudinal slot 204 configured to function as a window opening to trap hemorrhoids. The proximal portion 206 depends proximally from the main portion 202. The proximal portion 206 has handles 208 thereon configured to be manipulated by a user so as to adjust the cross sectional area of the proximal portion 206. The anoscope assembly 54 includes an anoscope sliding element (window) 122, anoscope return path plate 123, anoscope temperature sensor 124, anoscope return path cable 125, anoscope temperature sensor cable 126, anoscope return path connector 127, and anoscope temperature sensor connector 128.

The sliding element 122 is configured to slide through the proximal portion 206 and through the longitudinal slot 204 when the cross sectional area of the proximal portion 206 is sufficiently increased by a user by manipulation of the handles, thus providing access and secure placement of the sliding element 122 within the longitudinal slot.

The proximal portion 206 defines a broken away ring type structure separated from the main portion by a cutaway radial slot 207. It remains integrally connected to the main portion 202 by integrally connecting portion 209.

The anoscope body 121 is configured to be insertable into the human rectum. Thus, as described above, there is an opening on one side designed to trap hemorrhoids. The opening 204 is designed to fit and slide anoscope sliding element (window) 122. The anoscope body teeth 210 are configured to engage the anoscope sliding element teeth 136. The engagement of both teeth prevents the anoscope sliding window from backing out once it has pushed out distally. The anoscope body gap 133 is designed to make the area of the anoscope body where the anoscope body teeth 134 is attached moveable outward when the anoscope sliding window is removed from the anoscope body. Anoscope handles 208 can be used to move the body where the anoscope body tooth is attached outward. In the preferred embodiments shown in FIG. 5-5B (and in FIGS. 11-11B) the sliding element teeth 136 are angled and thus configured to be complementary operable with the proximal portion teeth 210 to provide insertion without manipulation of the handles. Manipulation of the handles is required to slide the sliding element in the reverse direction out from the proximal portion. The anoscope body is preferably but not necessarily made with transparent materials, for example, but not limited to polycarbonate, and acrylic, etc., for better viewing of the rectal wall for observation.

The length and diameter of the anoscope sliding window 122 are designed to fit the window opening of the anoscope 121. The anoscope sliding window is preferably but not necessarily made with transparent materials, for example, but not limited to polycarbonate, and acrylic, etc., for better viewing of the rectal wall for observation. Anoscope sliding window has an anoscope return path plate 123 attached to the distal end. Anoscope temperature sensor 124 is attached on or near the return path plate 123, where the temperature can be read tissue temperature at or adjacent to the return path plate 123. During ablation of hemorrhoid, the temperature read from the anoscope temperature sensor 124 may be the determining factor when to stop the procedure after completing it and/or interrupting it for safety. The temperature sensor 124 can be utilized using different temperature measuring modalities, for example, but not limited to thermocouples, thermistors, and RTDs. The anoscope temperature sensor cable 126 is attached to the anoscope temperature sensor 124. For the portion of the anoscope temperature sensor cable 126 that extends along the length of the anoscope sliding window 122, it is preferable but not limited to position the cable through the channel created inside of the sliding window. The other end of the anoscope temperature sensor cable 126 is attached to the anoscope temperature connector 128. In an embodiment that utilize thermocouples as the anoscope temperature sensor 124, the anoscope temperature cable 126 and anoscope temperature sensor 124 can be one assembly of thermocouple junction wire. The anoscope return path cable 125 is attached to the anoscope return path plate 123. For the portion of the anoscope return path cable 125 that extends along the length of the anoscope sliding window 122, it is preferable but not limited to position the cable through the channel created inside of the sliding window. The other end of the anoscope return path cable 125 is attached to the anoscope return path connector 127.

One end of the anoscope return path connector 127 is connected to the anoscope return path power cable 125, and the other end of the anoscope return path connector plugs into the system 55. The return path connector 127 has a portion that is electrically conductive that mates to electrically conductive material located inside of the system 55. The conductive material in the return path connector 127 is preferably not exposed to the user. Outside housing of the return path connector, 127 can be formed with dielectric materials, for example, but not limited to polycarbonate, ABS, and Nylon, etc.

In an embodiment of utilizing thermocouple wires as the return path temperature sensor 124, temperature sensing connector 128 is a thermocouple connector that matches the compound of the thermocouple wire used. In an embodiment of using a thermistor or RTD as temperature sensor 124, temperature sensing connector 128 is an electrical connector. One end of the temperature connector is attached to the temperature cable 126, and the other end plugs into the system 55.

For another embodiment of using resistive material 132 to deliver heat energy to hemorrhoid, the anoscope return path plate 123, the anoscope return path cable 125, and the anoscope return path connector 127 may not be necessary.

Referring to FIGS. 6A, 6B, 6C, 6D, 6E, 6F, and 6G, procedure steps using the ablation catheter 52 are illustrated. The steps include:

A) Insert anoscope body 121 into the rectum. For convenience, anoscope sliding element (window) 122 can be inserted into the window of the anoscope body 121 for better insertion into the rectum. Remove the anoscope sliding window 122 if inserted into the anoscope body 121. Position the hemorrhoid inside of the opening (window) of the anoscope body 121.

B) Slide the anoscope sliding window 122 into the window of the anoscope body 121 and trap hemorrhoid.

C) Mate dilator assembly 50 and dilator sheath assembly 51. Penetrate hemorrhoid.

D) Remove dilator assembly 50 from dilator sheath assembly 51 and attach syringe 129 to the dilator sheath. Remove trapped blood from the hemorrhoid using the syringe.

E) Remove syringe 129 from the dilator sheath and attach ablation catheter 52 to the dilator sheath. Ablate hemorrhoid.

F) Remove dilator sheath 51 and the ablation catheter 52.

G) Disengage the teeth 210 and 136 by moving the portion of the anoscope body 121 that is proximal to the user divided by the anoscope gap 207 by pulling the anoscope handles 208. Remove anoscope sliding window 122 from the anoscope body 121.

For another method of not using the dilator and removing trapped blood from hemorrhoid, after mating the ablation catheter 52 and dilator sheath 51, mated assembly of the ablation catheter and the dilator sheath can be penetrated inside of the hemorrhoid. Steps from C) through G) can be taken to proceed with the rest of the treatment.

Referring to FIGS. 7A, 7B, 7C, 7D, and 7E, procedure steps using the paddle ablation probe assembly 53 are illustrated. The steps include:

A) Insert anoscope body 121 into the rectum. For convenience, anoscope sliding window 122 can be inserted into the window of the anoscope body for better insertion into the rectum. Remove the anoscope sliding window 122 if inserted into the anoscope body. Position the hemorrhoid inside of the window of the anoscope body 121.

B) Slide the anoscope sliding body 122 and trap hemorrhoid.

C) Touch hemorrhoid using paddle ablation probe assembly 53 and ablate hemorrhoid.

D) Remove the paddle probe. Disengage the teeth 210 and 136 by moving the portion of the anoscope body 121 that is proximal to the user divided by the anoscope gap 133 by pulling the anoscope handles 208. Remove anoscope sliding window 122 from the anoscope body 121.

E) Remove anoscope.

Referring to FIG. 8, a system block diagram is illustrated of a preferred embodiment of the overall system for treating hemorrhoids, designated generally as 200. The system 200 uses an ablation control system assembly having microcontroller-based electronics capable of measuring different types of sensors as well as providing electric power to the ablation catheter and/or paddle probe. The power maybe, for example, RF power, DC power, or microwave power. System 55 includes ports to attach power output to the ablation catheter 52 or ablation paddle probe 53. The connection is made by attaching power connectors 110 or 119 to the system. System 55 also has a temperature sensing connection for the alation catheter temperature sensor 105 or paddle probe temperature sensor 114. The connection is made by attaching ablation catheter temperature connector 111 or the paddle probe temperature connector 120. It is preferable but not necessary to combine the power and temperature connectors into a one connector assembly both on the control system 55, and the catheter 52/paddle probe 53 for ease of operation. System 55 also has a return path connection for the anoscope 54. The connection is made by attaching return path power connector 127 into the system. The system also has a connection to the return path temperature sensor by attaching a temperature sensor connector 128 into the system. The system also has a connector to attach ground pad 130. It is preferable but not necessary to combine the power and temperature connectors into one connector assembly both on the system 55, and the anoscope 54 for ease of operation.

Figure 9A:
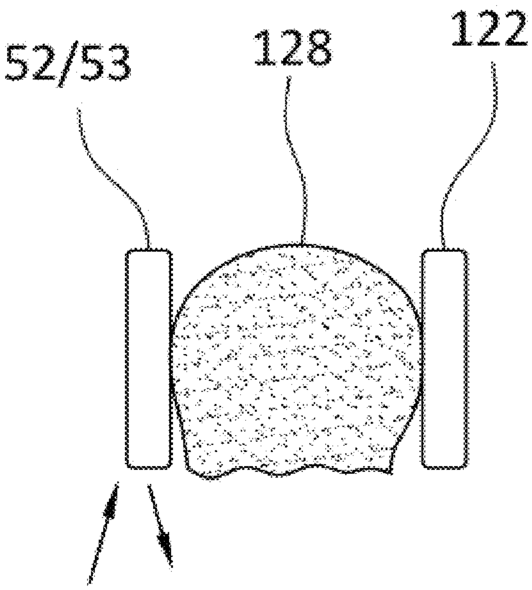
FIG. 9A is a block diagram of the current path of one embodiment.
Figure 9B:
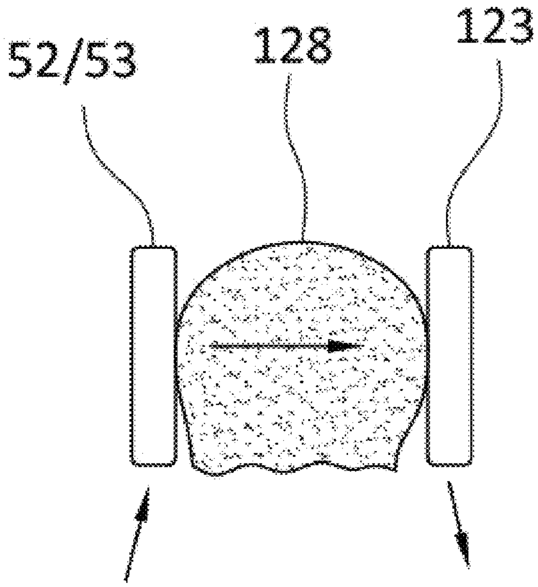
FIG. 9B is a block diagram of the current path of another embodiment.
Figure 9C:
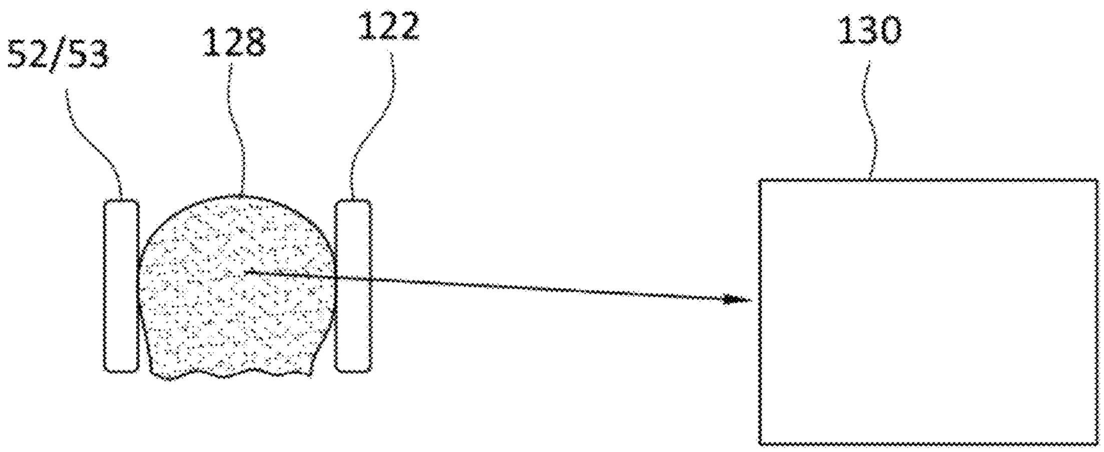
FIG. 9C is a block diagram of the current path of yet another embodiment.

When ground pad 130 is attached, the system will sense the connection and it can automatically operate the system as a monopolar system described in FIG. 9C. In this mode, the system will ignore the power connection between system 50 and the anoscope power connector 127 regardless of whether the connection is made or not.

When ground pad 130 is not attached, the system will sense the presence of the anoscope power connection 127 into the system. If the anoscope power connection is present, the system will operate the system as a bipolar system between the ablation catheter 52 or the paddle probe 53 and the anoscope return path pad. If the anoscope power connection is not present or the impedance between two poles described above is large at the time of the treatment, the system will operate the system as a resistive heating method and ignore the connection to the return path.

Ground pad 130 may or may not be needed based on the operating methods described in the following sections.

The user interface module assembly 140 is preferably a touch screen display used to communicate with the user in two ways. The screen displays the current status of the treatment as well as gives users valuable information during treatment, such as timer, temperature, power, voltage, current, or impedance information. It also provides user commands to the system by providing user clickable options. The system can also incorporate a treatment switch as a foot petal (not shown) and/or a button switch on the ablation catheter (or paddle probe) (not shown) to make it easier for the user to start and stop the procedure.

Referring to FIGS. 9A, 9B, and 9C, the diagram and current flow for several ablation methods are illustrated. The bar on the lefthand side represents ablation catheter 52 (or paddle probe 53). The circle in the middle represents a hemorrhoid 128. The bar on the right side represents the anoscope return path plate 122. The square represents ground pad 130. The arrows represent the current flow.

Referring to FIG. 9A, the non-electrically conductive ablation method (i.e. resistive heating mode) is illustrated. The ablation catheter 52 (or paddle probe 53) are activated using resistive material 132. Therefore, there is no current flow from the catheter and probe 52/53 to hemorrhoid or the adjacent tissue. Conductive heat transfer is used to deliver heat to hemorrhoids. The return path plate 122 is not needed for the current path. Temperature measurement is the only function required from the return path. It is ideal to limit how high the catheter 52 and/or probe 53 can reach in terms of temperature in order to prevent over treatment of the tissue adjacent to the catheter and probe. In order to do that, ablation catheter temperature sensor 105 or paddle probe temperature sensor 114 is monitored to control the current going into the resistive material from the system 55. An ideal safeguard is to limit the maximum time that the current can flow to the resistive material by means of a maximum duty cycle and/or total treatment time limitation. The anoscope temperature sensor 124 located at or near the return path plate 123 is used to determine whether ablation is completed throughout the hemorrhoid. When the targeted temperature is reached, system 55 will shut off the treatment.

Referring to FIG. 9B, a bipolar or return path plate mode is illustrated. The ablation catheter 52 (or paddle probe 53) are activated using RF or other methods that flow current from the source to the body. The current will flow from the ablation catheter 53 or paddle probe 53 to hemorrhoid 128, then to the return path plate 123. By minimizing the current flow distance from the catheter/probe to the return path plate, the energy requirement for treatment is relatively smaller compared to the method of using ground pad. In order to safeguard, it is ideal to limit the maximum time that the current can flow to hemorrhoids by means of maximum duty cycle and/or total treatment time limitation. It is also ideal to limit the maximum current that can flow into hemorrhoids. It can be achieved by impedance measurement of hemorrhoids and use a predetermined maximum current allowed to flow. The anoscope temperature sensor 124 located at or near the return path plate 123 is used to determine whether ablation is completed throughout hemorrhoid. When the targeted temperature is reached, system 55 will shut off the treatment.

Referring to FIG. 9C, a monopolar mode is illustrated. The ablation catheter 52 (or paddle probe 53) are activated using RF or other methods that flow current from the source to the body. The current will flow from the ablation catheter 53 (or paddle probe 53) to hemorrhoid 128, then to the ground pad attached further away from the return path pad. One of the possible issues with the method illustrated in FIG. 9B is that when the ablation and return path area are similar in size, usually the hottest area in terms of temperature is next to two poles. Since the temperature sensors are located near the two poles, it is possible that the two temperature sensors would present a temperature higher than the actual temperature of the hemorrhoid tissue; therefore, under treatment can occur. The method illustrated in FIG. 9C eliminates this issue by placing the ground pad away from the anoscope temperature sensor which is relatively distanced from the targeted area. Temperature sensor 105 or 114 is activated to control the power output. As a safeguard, it is ideal to limit the maximum time that the current can flow to hemorrhoids by means of a maximum duty cycle and/or total treatment time limitation. It is also ideal to limit the maximum current that can flow into hemorrhoids. Although power control based on impedance measurement is feasible with monopolar systems, real-time impedance measurement and power control is less precise with monopolar systems due to higher impedance measurements due to the distance between the source and return path of the energy. Temperature sensor 124 is used as a safety feature not to increase the temperature at the anoscope temperature sensor 124 above a certain temperature. In this method, since the anoscope temperature sensor 124 is in the current path rather than at the end, the temperature measured would be highly reflective of the temperature of hemorrhoid.

Figure 10:
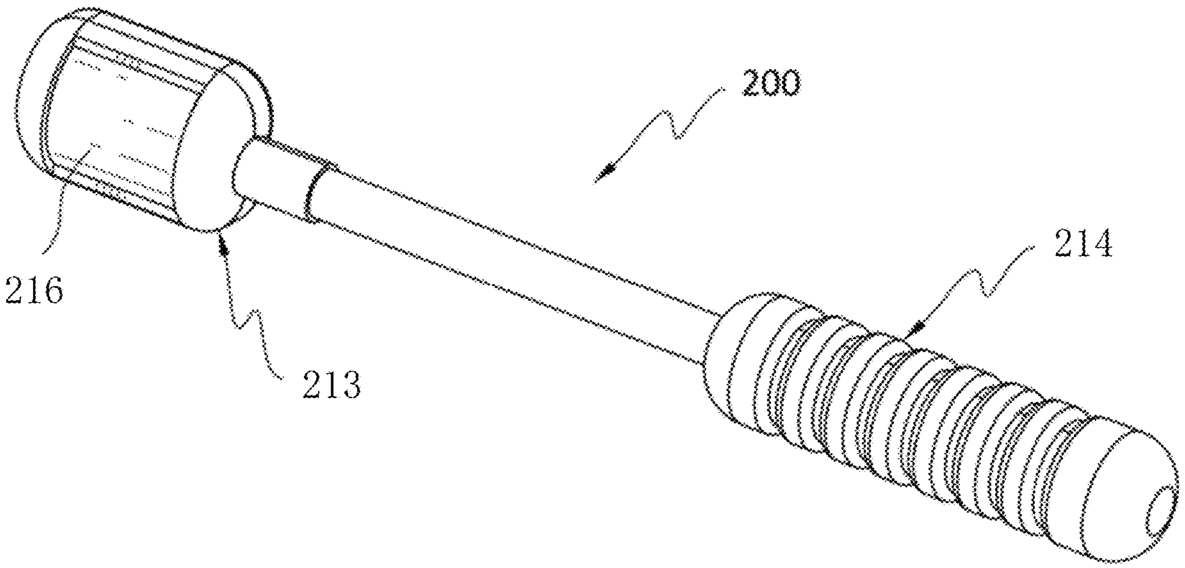
FIG. 10 is a front perspective view of another embodiment of the ablation probe (catheter).
Figure 10A:
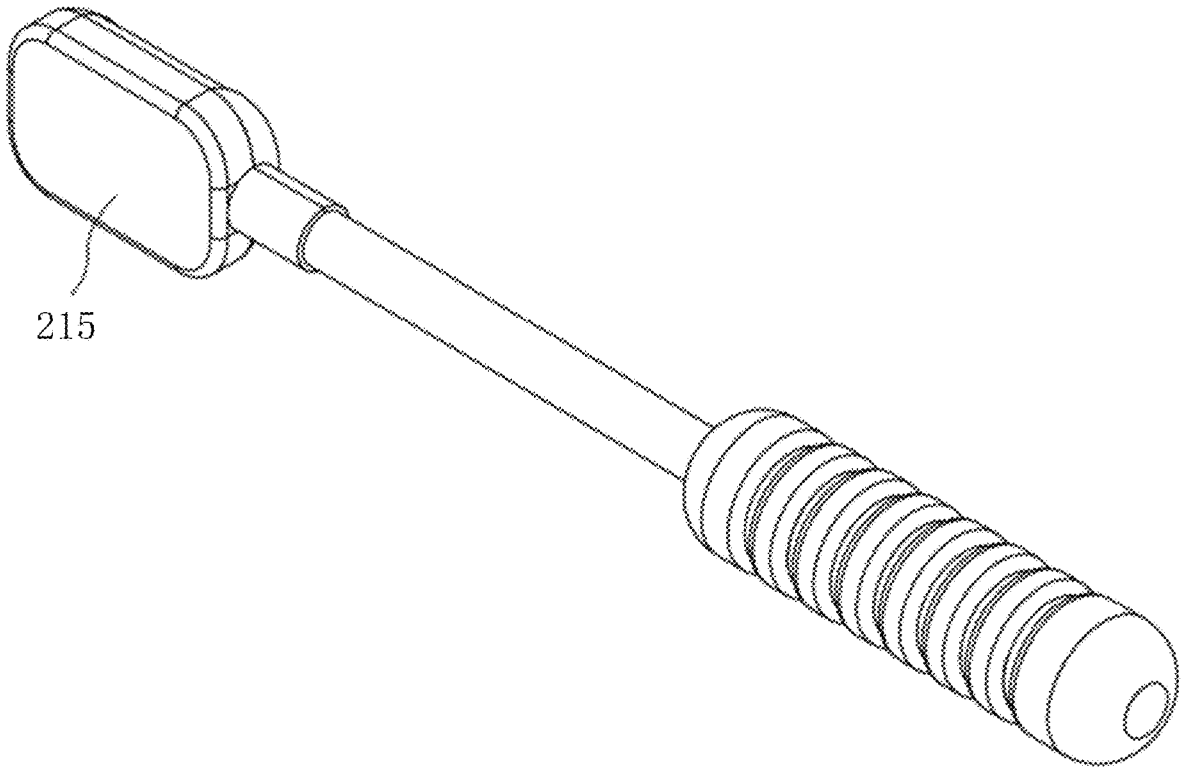
FIG. 10A is a rear perspective view of the ablation probe of FIG. 10.
Figure 10B:
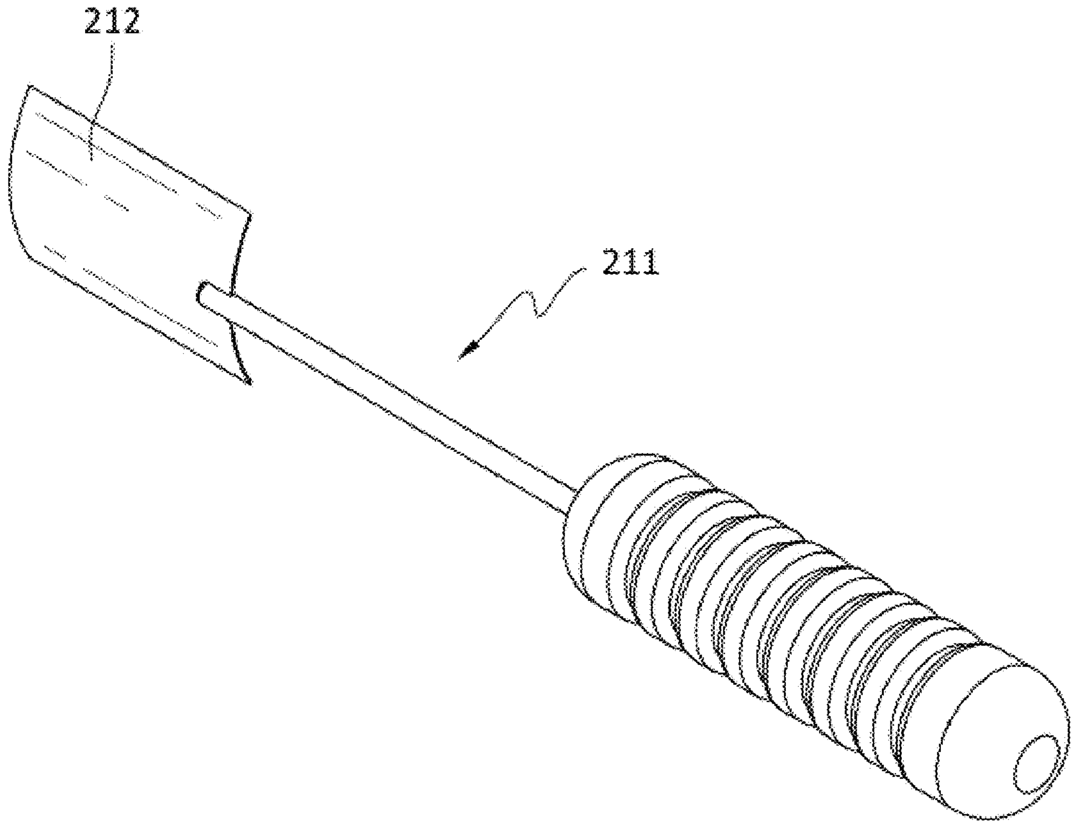
FIG. 10B is a perspective view of a thin paddle probe.

Referring now to FIGS. 10-10A, a first preferred embodiment of a treatment probe is illustrated, designated generally as 200, which includes a domed top ablation tip 213 on one end and a handle 214 on the other end. An ablation surface 215 opposes the dome shaped top surface 216. FIG. 10B illustrates a thin paddle probe, designated generally as 211. It includes an ablation surface 212 that can be a resistive or conductive surface. It can be active on both sides.

Figure 11:
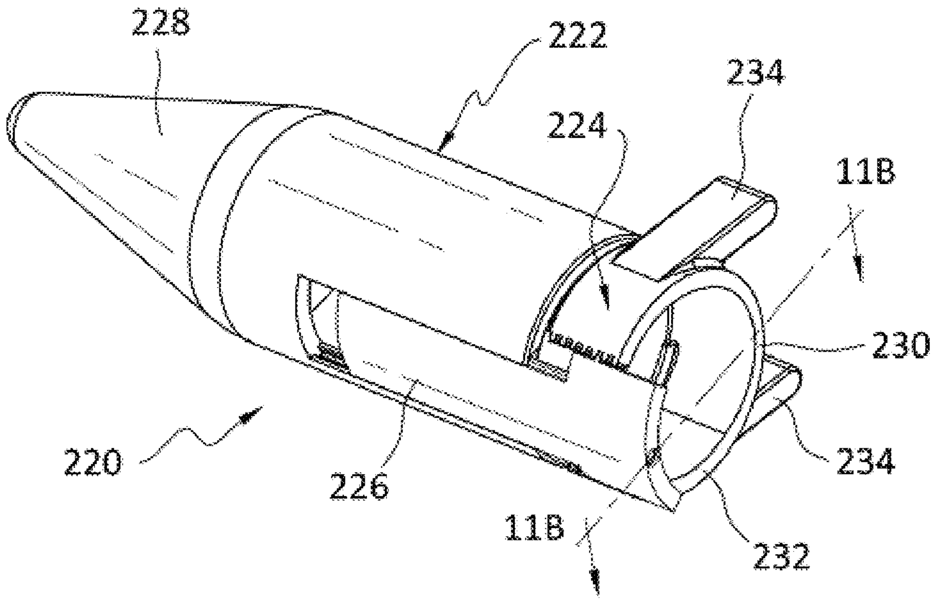
FIG. 11 is a perspective view of a preferred embodiment of the anoscope assembly in a nearly closed position.
Figure 11A:
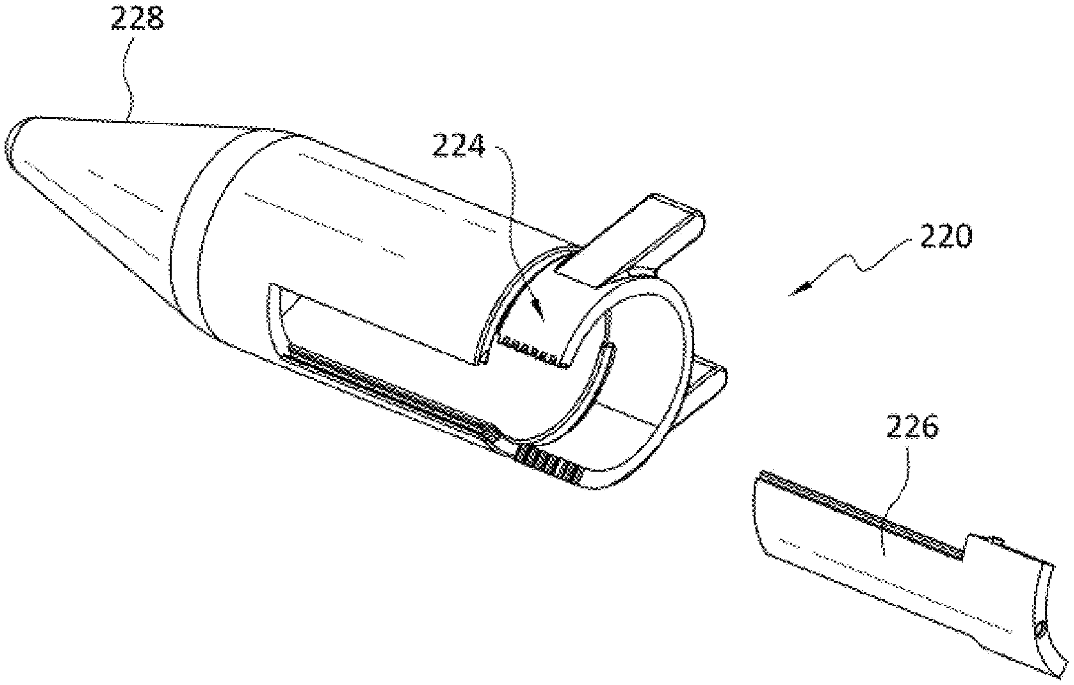
FIG. 11A is an exploded perspective view of the anoscope assembly of FIG. 11.
Figure 11B:
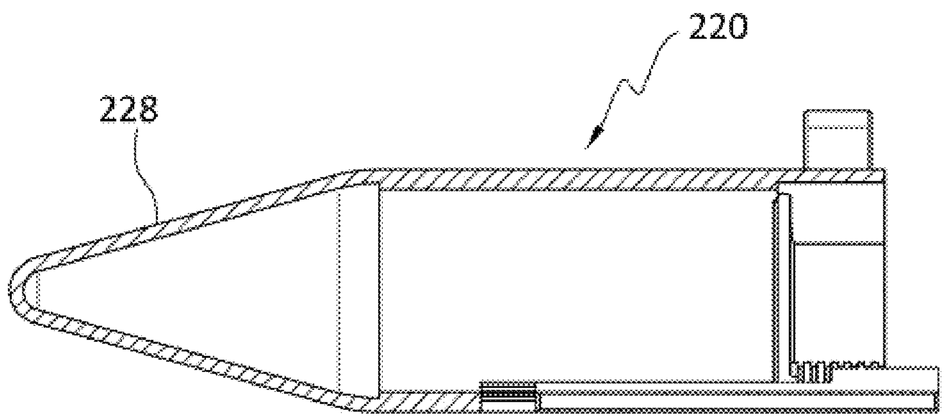
FIG. 11B is a view taken along line 11B-11B of FIG. 11.

Referring now to FIGS. 11-11B a preferred second embodiment of an anoscope assembly is illustrated, designated generally as 220. This embodiment includes the same salient features as the FIG. 5 embodiment. It includes a main portion 222, proximal portion 224, and sliding element 226. The tip 228 is also shown in this illustration. The proximal portion 224 preferably has a relatively thin section 230 and a relatively thick section 232 to enhance flexibility. The ears 234 descend tangentially from the surface of the proximal portion 224 to provide ease in use.

The different methods to treat after trapping the hemorrhoid can be described as follows;

1. Invasive Method One
 - a. Dilator and dilator sheath are place inside of the hemorrhoid.
 - b. Dilator is retracted leaving the sheath inside of the hemorrhoid.
 - c. Attach syringe on the sheath.
 - d. Draw blood out of the hemorrhoid to reduce the mass of the hemorrhoid.
 - e. Insert ablation probe into the sheath.
 - f. Apply RF emerge. The ablation probe becomes first polarity. The ablation probe also has temperature sensor inside to control the power output.
 - g. Return path (second polarity) is place on the sliding element of the anoscope assembly
 - h. The sliding element also has temperature sensor to be used to determine when the procedure is done.
2. Invasive Method Two (Monopolar)
 - a. Attach ground pad to the patients back or thigh.
 - b. Dilator and dilator sheath are place inside of the hemorrhoid.
 - c. Dilator is retracted leaving the sheath inside of the hemorrhoid.
 - d. Attach syringe on the sheath.
 - e. Draw blood out of the hemorrhoid to reduce the mass of the hemorrhoid.
 - f. Insert ablation probe into the sheath.
 - g. Apply RF emerge. The ablation probe becomes first polarity. The ablation probe also has temperature sensor inside to control the power output.
 - h. The sliding has temperature sensor to be used to determine when the procedure is done.
3. Non-Invasive Method One (Conductive heating)
 - a. Non-invasive conductive probe (paddle probe) is place on the top of the hemorrhoid.
 - b. Probe has heater element and temperature monitoring element within the probe to control the energy applied to the hemorrhoid.
 - c. The sliding element has temperature sensor to be used to determine when the procedure is done.
4. Non-Invasive Method Two (RF heating)
 - a. Non-invasive RF probe is place on the top of the hemorrhoid.
 - b. Apply RF emerge. The ablation probe becomes first polarity. The ablation probe also has temperature sensor inside to control the power output.
 - c. Return path (second polarity) is place on the sliding element of the anoscope assembly.
 - d. The sliding element also has temperature sensor to be used to determine when the procedure is done.
5. Non-Invasive Method Three (RF heating Monopolar)
 - a. Attach ground pad to the patients back or thigh.
 - b. Non-invasive RF probe is place on the top of the hemorrhoid.
 - c. Apply RF emerge. The ablation probe becomes first polarity. The ablation probe also has temperature sensor inside to control the power output.
 - d. The sliding has temperature sensor to be used to determine when the procedure is done It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more computers, computer processors, and/or other elements of a computer system. Such features are either impossible or impractical to implement mentally and/or manually. For example, embodiments of the present invention may read and write data to electronic memory devices (such as RFID tags) and/or to distributed ledgers (such as a blockchain), which are functions that cannot be performed mentally or manually.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element (s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

Any step or act disclosed herein as being performed, or capable of being performed, by a computer or other machine, may be performed automatically by a computer or other machine, whether or not explicitly disclosed as such herein. A step or act that is performed automatically is performed solely by a computer or other machine, without human intervention. A step or act that is performed automatically may, for example, operate solely on inputs received from a computer or other machine, and not from a human. A step or act that is performed automatically may, for example, be initiated by a signal received from a computer or other machine, and not from a human. A step or act that is performed automatically may, for example, provide output to a computer or other machine, and not to a human.

The invention claimed is:

1. A system for treating hemorrhoids, comprising:

a) an anoscope assembly, comprising:

i) an elongated anoscope body having a distal end and a proximal end, said anoscope body being configured to be insertable into the rectum of a patient, said elongated anoscope body, comprising:

1. a main portion having a longitudinal slot configured to function as a window opening to trap hemorrhoids;

2. a proximal portion depending proximally from said main portion, said proximal portion having handles thereon configured to be manipulated by a user so as to adjust the cross-sectional area of the proximal portion;

ii) a sliding element configured to slide through the proximal portion and through said longitudinal slot, thus providing access and secure placement of the sliding element within the longitudinal slot together with said elongated anoscope body; and, b) a treatment probe operably connected to said anoscope assembly, configured to provide energy to a hemorrhoid during treatment;

wherein:

a) said proximal portion defines a broken away ring type structure, the broken away ring type structure having proximal portion teeth on broken away edges thereof; and, b) said sliding element includes a sliding element proximal portion having sliding element teeth configured to be complementary operable with said proximal portion teeth to prevent relative movement therebetween.

2. The system of claim 1 further comprising an ablation control system assembly operatively connectable to said anoscope assembly.

3. The system of claim 1 wherein said elongated anoscope body and said sliding element are configured to provide access and placement of the sliding element without manipulation of the handles when the sliding element is being slid into the proximal portion, but manipulation of the handles is required to slide the sliding element in the reverse direction out from the proximal portion.

4. The system of claim 1 wherein said elongated anoscope body and said sliding element are configured to provide access and placement of the sliding element without manipulation of the handles when the sliding element is being slid into the proximal portion, but manipulation of the handles is required to slide the sliding element in the reverse direction out from the proximal portion; and, wherein:

a) said proximal portion defines a broken away ring type structure, the broken away ring type structure having proximal portion teeth on broken away edges thereof; and b) said sliding element includes a sliding element proximal portion having sliding element teeth configured to be complementary operable with said proximal portion teeth to provide insertion without manipulation of the handles, but manipulation of the handles is required to slide the sliding element in the reverse direction out from the proximal portion.

5. The system of claim 1, wherein said broken away ring type structure is integrally connected to said main portion.

6. The system of claim 1, wherein said handles comprise a pair of handles extending from said proximal portion.

7. The system of claim 1, wherein: said elongated anoscope body and said sliding element are configured to provide access and placement of the sliding element when the cross-sectional area of the proximal portion is sufficiently increased by a user by manipulation of said handles.

8. A method for treating hemorrhoids, comprising:

a) providing the system of claim 1;

b) inserting said anoscope assembly into the rectum;

c) inserting the treatment probe;

d) performing a treatment by utilizing the treatment probe; and e) removing the anoscope assembly.

9. The method of claim 8 further including the step of inserting a dilator assembly and a dilator sheath assembly after inserting said anoscope assembly and before said treatment probe.

10. The method of claim 8 said treatment is performed utilizing a resistive heating mode.

11. The method of claim 8 said treatment is performed utilizing a bipolar mode.

12. The method of claim 8 said treatment is performed utilizing a monopolar mode.

* * * * *